US007166765B2

(12) United States Patent
Lowe et al.

(10) Patent No.: US 7,166,765 B2
(45) Date of Patent: Jan. 23, 2007

(54) ISOLATED LEC1 TRANSCRIPTIONAL REGULATOR ENCODING NUCLEIC ACIDS AND METHODS OF USE THEREOF

(75) Inventors: Keith S. Lowe, Johnston, IA (US); William J. Gordon-Kamm, Urbandale, IA (US); Theodore M. Klein, Wilmington, DE (US); Sonriza Rasco-Gaunt, Wilmington, DE (US); Rebecca E. Cahoon, Webster Groves, MO (US); Xifan Sun, Urbandale, IA (US); George J. Hoerster, Des Moines, IA (US); Carolyn Gregory, Greenlawn, NY (US); Ramgopal Nadimpalli, Bloomfield, NJ (US); Yumin Tao, Urbandale, IA (US)

(73) Assignees: Pioneer Hi-Bred International, Inc., Johnston, IA (US); E. I. du Pont de Nemours and Company, Wilmington, DE (US)

( * ) Notice: Subject to any disclaimer, the term of this patent is extended or adjusted under 35 U.S.C. 154(b) by 66 days.

(21) Appl. No.: 10/744,620

(22) Filed: Dec. 22, 2003
(Under 37 CFR 1.47)

(65) Prior Publication Data
US 2005/0034193 A1 Feb. 10, 2005

Related U.S. Application Data

(62) Division of application No. 09/435,054, filed on Nov. 8, 1999, now Pat. No. 6,825,397.

(60) Provisional application No. 60/107,810, filed on Nov. 10, 1998, provisional application No. 60/107,643, filed on Nov. 9, 1998.

(51) Int. Cl.
C12N 15/09 (2006.01)
C12N 15/29 (2006.01)
C12N 15/82 (2006.01)
A01H 5/00 (2006.01)

(52) U.S. Cl. ............... 800/278; 800/298; 800/295; 800/320.1; 800/317; 536/23.6; 435/320.1; 435/468; 435/69.1

(58) Field of Classification Search ........... 800/278, 800/298, 295; 536/23.6; 435/69.1, 468, 435/320.1
See application file for complete search history.

(56) References Cited

U.S. PATENT DOCUMENTS 5,811,636 A 9/1998 Hanna et al.
6,235,975 B1 5/2001 Harada et al.

6,320,102 B1 11/2001 Harada et al.
6,781,035 B1 8/2004 Harada et al.

FOREIGN PATENT DOCUMENTS

WO WO 98/37181 A1 8/1998
WO WO 99/67405 A2 12/1999

OTHER PUBLICATIONS

Parcy et al. The Plant Cell, vol. 9, pp. 1265-1277 (1997).*
Lotan et al. Cell, vol. 93, pp. 1195-1205 (1998).*
Bellorini et al., CCAAT binding NF-Y-TBP interactions; NF-YB and NF-YC require short domains adjacent to their histone fold motifs for association with TBP basic residues, Nucleic Acids Research 25(11):2174-2181 (1997).
Edwards et al., Multiple Genes Encoding the Conserved CCAAT-Box Transcription Factor-Complex Are Expressed in Arabidopsis, Plant Physiol. 117:1015-1022 (1988).
Lotan et al., Arabidopsis Leafy Cotyledon1 is Sufficient to Induce Embryo Development in Vegetative Cells, Cell 91:1195-1205 (1998).
Sasaki, T., Accession No. C19737, Rice EST, EBI Database (1996).
Sasaki, T., Accession No. C28028. Rice EST, EBI Database (1997).
West et al., Leafy Cotyledon1 is an Essential Regulator of Late Embryogenesis and Cotyledon Identify in Arabidopsis, Plant Cell 6:1731-1745 (1994).
Parcy et al., The Abscisic Acid-Insensitives, FUSCA3 and Leafy Cotyledon1 Loci Act in Concert to Control Multiple Aspects of Arabidopsis Seed Development, Plant Cell 9:1265-1277 (1997).
Ohad et al., A mutation that allows endosperm development without fertilization, Proc. Natl. Acad. Sci. USA 93:5319-5324 (1996).
Shoemaker et al., Accession No. A1495007, Soybean EST, EBI Database (1999).
Li et al., Accession No. X59714, CAAT-box DNA binding protein, NCBI Database (1992).
Bork, P., Powers and Pitfalls in Sequence Analysis: The 70% Hurdle, Genome Research 10:398-400 (2000).

(Continued)

Primary Examiner—Medina A. Ibrahim
(74) Attorney, Agent, or Firm—Pioneer Hi-Bred International, Inc.

(57) ABSTRACT

The invention provides isolated nucleic acids and their encoded proteins which act as transcriptional activators and methods of use thereof. The invention further provides expression cassettes, transformed host cells, transgenic plants and plant parts.

13 Claims, 1 Drawing Sheet

OTHER PUBLICATIONS

Lazar et al., Transforming Growth Factor Alpha: Mutation of Aspartic Acid 47 and Leucine 48 Results in Different Biological Activities, Molecular and Cellular Biology 8(3):1247-1252 (1988).
Sequence Search Result, Accession No. Y11210 (1997).

Broun et al., Catalytic Plasicity of Fatty Acid Modification Enzymes Underlying Chemial Diversity of Plant Lipids, Science 282:1315-1317 (1998).

* cited by examiner

Figure 1

```
Arabidopsis   REQDQYMPIANVIRIMRKTLPSHAKISDDAKETIQECVSEYISFVTGEANERCQREQRKTITAEDILWAMSKLGFDNYVDPLTVFINRYR
Soybean       REQDQYMPIANVIRIMRRILPAHAKISDDAKETIQECVSEYISFITAEANERCQREQRKTVTAEDVLWAMEKLGFDNYAHPLSLYLHRYR
Soybean       REQDRFMPIANVIRIMRKILPPHAKISDDAKETIQECVSEYISFITGEANERCQREQRKTITAEDVLWAMSKLGFDDYIEPLTMYLHRYR
Soybean       REQDRFMPIANVIRIMRKILPPHAKISDDAKETIQECVSEYISFITGEANERCQREQRKTITAEDVLWAMSKLGFDDYIEPLTMYLHRYR
Maize         REQDRLMPIANVIRIMRRVLPAHAKISDDAKETIQECVSEYISFITGEANERCQREQRKTITAEDVLWAMSRLGFDDYVEPLGAYLHRYR
A.mexicana    REQDRYMPIANVIRIMRKVLPTHAKISDDAKETIQECVSEYISFITSEANDRCQREQRKTITAEDVLWAMSKLGXDEYIEPLTLYLQRYR
Vernonia      REQDRFMPIANVIRIMRKILPPHAKISDDAKETIQECVSEYISFVTGEANDRCQREQRKTITAEDVLWAMSKLGFDDYIEPLTVYLHRYR
Wheat         REQDRLMPIANVIRIMRRALPAHAKISDDAKEAIQECVSEFISFVTGEANERCRMQHRKTVNAEDIVWALNRLGFDDYVVPLSVL
Maize         REQDRLMPVANVSRIMRQVLPPYAKISDDAXEVIQELLFGISSLSWRGETKRCHTERRKTVTSEDIVWAMSRLGFDDYVAPLGAFLQRMR
Maize                                                       ARGKTVTSEDIVWAMSRLGFDDYVAPLGAFLQRMR
```

ISOLATED LEC1 TRANSCRIPTIONAL REGULATOR ENCODING NUCLEIC ACIDS AND METHODS OF USE THEREOF

CROSS-REFERENCE TO RELATED APPLICATIONS

This is a divisional application that claims priority to U.S. application Ser. No. 09/435,054 filed Nov. 8, 1999 now U.S. Pat. No. 6,825,397; U.S. Provisional Applications Ser. No. 60/107,643 filed Nov. 9, 1998 and U.S. Provisional Application No. 60/107,810 filed Nov. 10, 1998.

TECHNICAL FIELD

The present invention relates generally to plant molecular biology. More specifically, it relates to nucleic acids and methods for modulating their expression in plants.

BACKGROUND OF THE INVENTION

Major advances in plant transformation have occurred over the last few years. However, in major crop plants, such as maize and soybeans, serious genotype limitations still exist. Transformation of agronomically important maize inbred lines continues to be both difficult and time consuming. Traditionally, the only way to elicit a culture response has been by optimizing medium components and/or explant material and source. This has led to success in some genotypes, but most elite hybrids fail to produce a favorable culture response. While, transformation of model genotypes is efficient, the process of introgressing transgenes into production inbreds is laborious, expensive and time consuming. It would save considerable time and money if genes could be introduced into and evaluated directly in commercial hybrids.

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. (Reference Bowen et al, *Third International Congress of the International Society for Plant Molecular Biology*, 1991, Abstract 1093). Therefore it would be desirable to provide improved methods capable of increasing transformation efficiency in a number of cell types.

Typically a selectable marker is used to recover transformed cells. Traditional selection schemes expose all cells to a phytotoxic agent and rely on the introduction of a resistance gene to recover transformants. Unfortunately, the presence of dying cells may reduce the efficiency of stable transformation. It would therefore be useful to provide a positive selection system for recovering transformants.

In spite of increases in yield and harvested area worldwide, it is predicted that over the next ten years, meeting the demand for corn will require an additional 20% increase over current production (Dowswell, C. R., Paliwal, R. L., Cantrell, R. P., 1996, Maize in the Third World, Westview Press, Boulder, Colo.).

In hybrid crops, including grains, oil seeds, forages, fruits and vegetables, there are problems associated with the development and production of hybrid seeds. The process of cross-pollination of plants is laborious and expensive. In the cross-pollination process, the female plant must be prevented from being fertilized by its own pollen. Many methods have been developed over the years, such as detasseling in the case of corn, developing and maintaining male sterile lines, and developing plants that are incompatible with their own pollen, to name a few. Since hybrids do not breed true, the process must be repeated for the production of every hybrid seed lot.

To further complicate the process, inbred lines are crossed. For example in the case of corn, the inbreds can be low yielding. This provides a major challenge in the production of hybrid seed corn. In fact, certain hybrids cannot be commercialized at all due to the performance of the inbred lines. The production of hybrid seeds is consequently expensive, time consuming and provides known and unknown risks. It would therefore be valuable to develop new methods which contribute to the increase of production efficiency of hybrid seed.

As new traits are added to commercial crops by means of genetic engineering, problems arise in "stacking" traits. In order to develop heritable stacked traits, the traits must be linked because of segregating populations. Improved methods for developing hybrid seed which would not require linking of the traits would significantly shorten the time for developing commercial hybrid seeds.

Gene silencing is another problem in developing heritable traits with genetic engineering. Frequently gene silencing is seen following meiotic divisions. Elimination or reduction of this problem would advance the state of science and industry in this area.

SUMMARY OF THE INVENTION

It is the object of the present invention to provide nucleic acids and polypeptides relating to embryogenesis.

It is another object of the present invention to provide nucleic acids and polypeptides that can be used to identify interacting proteins involved in transcription regulation in embryogenesis.

It is another object of the present invention to provide antigenic fragments of the polypeptides of the present invention.

It is another object of the present invention to provide transgenic plants and plant parts containing the nucleic acids of the present invention.

It is another object of the present invention to provide methods for modulating, in a transgenic plant, the expression of the nucleic acids of the present invention.

It is another object of the present invention to provide a method for improving transformation frequencies.

It is another object of the present invention to provide a method for improving transformation efficiency in cells from various sources.

It is another object of the present invention to provide a method for a positive selection system.

It is another object of the present invention to provide a method for efficiently producing hybrid seed via apomixis.

It is another object of the present invention to provide a method for stacking traits which does not require linking of traits.

It is another object of the present invention to provide a method for reducing the problem of gene silencing.

The present invention relates to a HAP3-type CCAAT-box binding transcriptional activator polynucleotides and polypeptides, and in particular, the leafy cotyledon 1 transcriptional activator (LEC1) polynucleotides and polypeptides. In other aspects the present invention relates to expression cassettes optionally linked in antisense orientation, host cells transfected with at least one expression cassette, and transgenic plants and seeds comprising the expression cassettes. Further aspects of the invention include methods of using the polynucleotides and polypeptides. In a further aspect, the present invention relates to a method of modulating expression of the polynucleotides encoding the polypeptides of the present invention in a plant. Expression of the polynucleotides encoding the proteins of the present invention can be increased or decreased relative to a non-transformed control plant.

DETAILED DESCRIPTION OF THE INVENTION

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "nucleic acid" means a polynucleotide and includes single or double-stranded polymer of deoxyribonucleotide or ribonucleotide bases. Nucleic acids may also include modified nucleotides that permit correct read through by a polymerase and do not alter the expression of a polypeptide encoded by the polynucleotide.

As used herein, "LEC1 nucleic acid" means a nucleic acid or polynucleotide that codes for a LEC1 polypeptide.

As used herein, "polypeptide" means proteins, protein fragments, modified proteins, amino acid sequences and synthetic amino acid sequences. The polypeptide can be glycosylated or not.

As used herein, "LEC1 polypeptide" means a HAP3 family member, CCAAT-box binding transcriptional activator polypeptide that regulates gene expression during embryo development, and that contains the conserved sequence set out in SEQ ID NO: 23.

As used herein, "plant" includes plants and plant parts including but not limited to plant cells, plant tissue such as leaves, stems, roots, flowers, and seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid. Alternatively, fragments of a nucleotide sequence that are useful as hybridization probes generally do not encode fragment proteins retaining biological activity. Thus, fragments of a nucleotide sequence are generally greater than 20, 30, 50, 100, 150, 200 or 300 nucleotides and up to the entire nucleotide sequence encoding the proteins of the invention. Generally the probes are less than 1000 nucleotides and preferably less than 500 nucleotides. Fragments of the invention include antisense sequences used to decrease expression of the inventive polynucleotides. Such antisense fragments may vary in length ranging from at least about 20 nucleotides, about 50 nucleotides, about 100 nucleotides, up to and including the entire coding sequence.

By "functional equivalent" as applied to a polynucleotide or a protein is intended a polynucleotide or a protein of sufficient length to modulate the level of LEC1 protein activity in a plant cell. A polynucleotide functional equivalent can be in sense or antisense orientation.

By "variants" is intended substantially similar sequences. Generally, nucleic acid sequence variants of the invention will have at least 60%, 65%, or 70%, preferably 75%, 80% or 90%, more preferably at least 95% and most preferably at least 98% sequence identity to the native nucleotide sequence, wherein the % sequence identity is based on the entire sequence and is determined by GAP analysis using Gap Weight of 50 and Length Weight of 3. Generally, polypeptide sequence variants of the invention will have at least about 50%, 55%, 60%, 65%, 70%, 75% or 80%, preferably at least about 85% or 90%, and more preferably at least about 95% sequence identity to the native protein, wherein the % sequence identity is based on the entire sequence and is determined by GAP analysis using Gap Weight of 12 and Length Weight of 4.

A "responsive plant cell" or "responsive host cell" refers to a cell that exhibits a positive response to the introduction of LEC1 polypeptide or LEC1 polynucleotide compared to a cell that has not been introduced with LEC1 polypeptide or LEC1 polynucleotide. The response can be to enhance tissue culture response, induce somatic embryogenesis, induce apomixis, increase transformation efficiency or increase recovery of regenerated plants.

A "recalcitrant plant cell" is a responsive plant cell that generally does not exhibit a positive response such as tissue culture response, transformation efficiency or recovery of regenerated plants.

Nucleic Acids

The present invention relates to a HAP3-type CCAAT-box binding transcriptional activators, and in particular, the leafy cotyledon 1 transcriptional activator (LEC1). Expression of the LEC1 polynucleotide initiates formation of embryo-like structures and improves growth and recovery of transformants. The term apomixis is used to describe asexual reproduction that replaces or substitutes sexual methods of reproduction. When apomixis occurs, embryos are produced from maternal tissue and use only the maternal genome.

In particular the present invention relates to an isolated nucleic acid comprising a member selected from the group consisting of:
  (a) a polynucleotide which encodes a polypeptide of SEQ ID NO: 2, 8, 10, 12, 14, 16, 18, 20, or 22;
  (b) a polynucleotide amplified from a plant nucleic acid library using the primers of SEQ ID NOS: 3 and 4, 5 and 6, 9 and 10, or 11 and 12 or primers determined by using Vector nti Suite, InforMax Version 5.
  (c) a polynucleotide comprising at least 20 contiguous bases of SEQ ID NO: 1, 7, 9, 11, 13, 15, 17, 19, or 21;
  (d) a polynucleotide encoding a plant HAP3-type ccaat-box transcriptional activator with the conserved motif of SEQ ID NO: 23, wherein the polynucleotide is from a plant other than *Arabidopsis*;
  (e) a polynucleotide having at least 60% sequence identity to SEQ ID NO: 1, 9, 11, 13, 17, or 21 or 65% sequence identity to SEQ ID NO: 15 or 19 or 70% sequence identity to SEQ ID NO: 7, wherein the % sequence identity is based on the entire sequence and is determined by GAP analysis using Gap Weight of 50 and Length Weight of 3;

(f) a polynucleotide comprising at least 25 nucleotides in length which hybridizes under high stringency conditions to a polynucleotide having the sequence set forth in SEQ ID NO: 1, 7, 9, 11, 13, 15, 17, 19, or 21;

(g) a polynucleotide encoding the protein of SEQ ID NO: 2, 8, 10, 12, 14, 16, 18, 20, or 22, wherein the polynucleotide is from a plant other than *Arabidopsis;*

(h) a polynucleotide having the sequence set forth in SEQ ID NO: 1, 7, 9, 11, 13, 15, 17, 19, or 21; and (i) a polynucleotide complementary to a polynucleotide of (a) through (h).

In many cases of apomixis maternal tissues such as the nucellus or inner integument "bud off" producing somatic embryos. These embryos then develop normally into seed. Since meiosis and fertilization are circumvented, the plants developing from such seed are genetically identical to the maternal plant. Expression of the leafy cotyledon 1 gene in the nucellus integument, or cell specific expression in the megaspore mother cell would trigger embryo formation from maternal tissues.

Producing a seed identical to the parent has many advantages. For example high yielding hybrids could be used in seed production to multiply identical copies of high yielding hybrid seed. This would greatly reduce seed cost as well as increase the number of genotypes which are commercially available. Genes can be evaluated directly in commercial hybrids since the progeny would not segregate. This would save years of back crossing.

Apomixis would also provide a method of containment of transgenes when coupled with male sterility. The construction of male sterile autonomous agamospermy would prevent genetically engineered traits from hybridizing with weedy relatives.

Gene stacking would be relatively easy with apomixis. Hybrids could be successively re-transformed with various new traits and propagated via apomixis. The traits would not need to be linked since apomixis avoids the problems associated with segregation.

Apomixis can provide a reduction in gene silencing. Gene silencing is frequently seen following meiotic divisions. Since meiotic divisions never occur, it may be possible to eliminate or reduce the frequency of gene silencing. Apomixis can also be used stabilize desirable phenotypes with complex traits such as hybrid vigor. Such traits could easily be maintained and multiplied indefinitely via apomixis.

The Cauliflower Mosaic Virus 35S promoter has been used to overexpress LEC1 during *Agrobacterium*-mediated in planta transformation of *Arabidopsis* (Harada et al., WO 98/37184). As pointed out by Harada et al., 35S is a strong promoter, and in their experiments it was found that 35S: LEC1 did not improve transformation and actually appeared to hinder it (transformation efficiency with 35S:LEC1 was estimated to be 0.6% of that obtained normally). Thus, overexpression in a cell type such as those in the gametophytic stage of development may be inappropriate and detrimental to the transformation process and successful recovery of transformed progeny. In contrast, we have shown that ectopic expression of the LEC1 gene under the appropriate control elements (including tissue specific and/or inducible promoters) and in the appropriate plant cells can be used to stimulate embryo formation in tissues/genotypes normally not amenable to culture. Likewise ectopic expression in genotypes amenable to culture can increase the number of embryo precursor cells (or increase the number that develop into embryos) leading to an increase in transformation frequency. Transient expression using RNA or protein may be sufficient to initiate the cascade of events leading to embryo formation. This would be valuable in such target tissues as maize scutella, immature leaf bases, immature tassels, etc. The LEC1 gene could be used as a positive selectable marker, i.e. triggering embryogenesis in transgenic cells without killing the surrounding wild-type cells. This would happen since the cells receiving the introduced gene would undergo embryogenesis or in tissues already undergoing embryogenesis LEC1 expression would stimulate more rapid reiteration of somatic embryos.

It has been shown through sequence similarity that the *Arabidopsis* LEC1 polypeptide is homologous to the HAP3 subunit of the "CCAAT-box binding factor" class of eukaryotic transcriptional activators (Lotan et al., 1998, Cell 93:1195–1205). This class of proteins, which consist of Hap2/3/4 and 5, form a heteroligomeric transcriptional complex, that appears to activate specific gene sets in eukaryotes. Certain members of this family such as Hap2 and Hap5 appear to be ubiquitously expressed, while different Hap3 members are under developmental or environmental regulation. Plant HAP3 polypeptides can be recognized by a high degree of sequence identity to other HAP3 homologs in the "B domain" of the protein. For example, the B domain for the *Arabidopsis* LEC1, from amino acid residue 28 to residue 117, shares between 55% and 63% identity (75–85% similarity) to other members of the HAP3 family, including maize (HAP3), chicken, lamprey, *Xenopus*, human, mouse, *Emericella nidulens, Schizosaccharomyces pombe, Saccharomyces cerevisiae* and *Kluuyveromyces lactis* (Lotan et al., 1998).

Expression of the LEC1 gene in transformed cells initiates embryo development and stimulates development of pre-existing embryos. Normally, LEC1 expression is necessary for proper embryo maturation in the latter stages of embryo development, and LEC1 transgene expression thus may also promote these processes. The combined effect of these impacts on somatic embryogenesis is not only to stimulate growth of transformed cells, but also to insure that transformed somatic embryos develop in a normal, viable fashion (increasing the capacity of transformed somatic embryos to germinate vigorously). Continued ectopic overexpression beyond embryo maturation may negatively impact germination and vegetative plant growth (which may necessitate down-regulation of the LEC1 transgene during these stages of development.

Expression of the LEC1 gene will stimulate growth in cells with the potential to initiate or maintain embryogenic growth. Cells in established meristems or meristem-derive cell lineages may be less prone to undergo the transition to embryos. In addition, transformation methods that target certain reproductive tissues (or cells) such as vacuum-infiltration of *Agrobacterium* into *Arabidopsis* may have detrimental effects on recovery of transformants (triggering genes associated with embryogenesis may disrupt the proper functioning of these cells).

The polypeptides encoded by the present plant LEC1 genes can be distinguished from non-LEC HAP3 proteins by using the diagnostic motif shown in SEQ ID NO: 23.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, *sorghum,* barley, wheat, millet, or rice. Preferred dicots include soybeans, sunflower, canola, alfalfa, potato, or cassava.

Functional fragments included in the invention can be obtained using primers which selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical Approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alters, adds or deletes a single amino acid or a small percentage of amino acids in the encoded sequence is a "conservatively modified variant" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., Proc. Natl. Acad. Sci. USA 94:4504–4509 (1997).

The present invention also includes the use of 5' and/or 3' UTR regions for modulation of translation of heterologous coding sequences. Positive sequence motifs include translational initiation consensus sequences (Kozak, Nucleic Acids Res. 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12:387–395 (1984)) or MacVector 4.1 (Eastman Kodak Co., New Haven, Conn.).

For example, the inventive nucleic acids can be optimized for enhanced expression in plants of interest. See, for example, EPA0359472; WO91/16432; Perlak et al. (1991) Proc. Natl. Acad. Sci. USA 88:3324–3328; and Murray et al. (1989) Nucleic Acids Res. 17:477–498. In this manner, the polynucleotides can be synthesized utilizing plant-preferred codons. See, for example, Murray et al. (1989) Nucleic Acids Res. 17:477–498, the disclosure of which is incorporated herein by reference.

The present invention provides subsequences comprising isolated nucleic acids containing at least 16 contiguous bases of the inventive sequences. For example the isolated nucleic acid includes those comprising at least 16, 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391 and 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., Genomics, 37:327–336 (1996). Other methods for producing full-length libraries are known in the art. See, e.g., Edery et al., Mol. Cell Biol. 15(6):3363–3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, Nucl. Acids. Res. 18(19):5705–5711 (1990); Patanjali et al., Proc. Natl. Acad. U.S.A. 88:1943–1947 (1991); U.S. Pat. Nos. 5,482,685 and 5,637,685; and Soares et al., Proc. Natl. Acad. Sci. USA 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, Technique 3(2):58–63 (1991); Sive and St. John, Nucl. Acids Res. 16(22):10937 (1988); *Current Protocols in Molecular Biology*, Ausubel et al., Eds., Greene Publishing and Wiley-Interscience, New York (1995); and, Swaroop et al., Nucl. Acids Res. 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

For purposes of defining the invention the following conditions are provided. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 *"Overview of principles of hybridization and the strategy of nucleic acid probe assays"*, Elsevier, New York (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. BioTechniques 22(3): 481–486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues. Good results have been obtained using mitotically active tissues such as shoot meristems, shoot meristem cultures, embryos, callus and suspension cultures, immature ears and tassels, and young seedlings. The cDNAs of the present invention were obtained from immature zygotic embryo and regenerating callus libraries.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., Meth. Enzymol. 68:90–99 (1979); the phosphodiester method of Brown et al., Meth. Enzymol. 68:109–151 (1979); the diethylphosphoramidite method of Beaucage et al., Tetra. Lett. 22:1859–1862 (1981); the solid phase phosphoramidite triester method described by Beaucage and Caruthers, Tetra. Letts. 22(20):1859–1862 (1981), e.g., using an automated synthesizer, e.g., as described in Needham-VanDevanter et al., Nucleic Acids Res. 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The nucleic acids of the present invention include those amplified using the following primer pairs: SEQ ID NOS: 3–6 and 9–12.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual*; Cold Spring Harbor, N.Y. (1989); Gelvin et al.; *Plant Molecular Biology Manual* (1990); *Plant Biotechnology: Commercial Prospects and Problems*, eds. Prakash et al.; Oxford & IBH Publishing Co.; New Delhi, India; (1993); and Heslot et al.; *Molecular Biology and Genetic Engineering of Yeasts*; CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakayama et al., 1992, FEBS Lett 30:167–170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; Plant Sci. 47:95–102 (1986) and Reina, M., Ponte, I., Guillen, P., Boronat, A. and Palau, J., Sequence analysis of a genomic clone encoding a Zc2 protein from *Zea mays* W64 A, Nucleic Acids Res. 18(21): 6426 (1990). See the following site relating to the waxy promoter: Kloesgen, R. B., Gierl, A., Schwarz-Sommer, Z. S. and Saedler, H., Molecular analysis of the waxy locus of *Zea mays*, Mol. Gen. Genet. 203:237–244 (1986). The disclosures each of these are incorporated herein by reference in their entirety.

Preferably a weak constitutive promoter, such as the Nos promoter, an inducible promoter, such as In2, or a nucellus-preferred or integument-preferred promoter are used to induce apospory. For example the barley or maize Nuc1 promoter, the maize Cim 1 promoter or the maize LTP2 promoter can be used to preferentially express in the nucellus. See for example U.S. Ser. No. 60/097,233 filed Aug. 20, 1998 the disclosure of which is incorporated herein by reference.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8:4395–4405 (1988); Callis et al., Genes Dev. 1:1183–1200 (1987). Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron. While useful in conjunction with the above antibiotic and herbicide-resistance selective markers (i.e. use of the LEC1 gene can increase transformation frequencies when using chemical selection), a prefered use of LEC1 expression takes advantage of this gene conferring a growth advantage to transformed cells without the need for inhibitory compounds to retard non-transformed growth. Thus, LEC1 transformants are recovered based solely on their differential growth advantage.

Typical vectors useful for expression of genes in higher plants are well known in the art and include vectors derived from the tumor-inducing (Ti) plasmid of *Agrobacterium tumefaciens* described by Rogers et al., Meth. In Enzymol. 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. USA 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., Proc. Natl. Acad. Sci. USA 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2:279–289 (1990) and U.S. Pat. No. 5,034,323.

Recent work has shown suppression with the use of double stranded RNA. Such work is described in Tabara et al., Science 282:5388:430–431 (1998).

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., Nature 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res (1986) 14:4065–4076, describe covalent bonding of a single-stranded DNA fragment with alkylating derivatives of nucleotides complementary to target sequences. A report of similar work by the same group is that by Knorre, D. G., et al., Biochimie (1985) 67:785–789. Iverson and Dervan also showed sequence-specific cleavage of single-stranded DNA mediated by incorporation of a modified nucleotide which was capable of activating cleavage (J. Am. Chem. Soc. (1987) 109:1241–1243). Meyer, R. B., et al., J. Am. Chem. Soc. (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197–3203. Use of crosslinking in triple-helix forming probes was also disclosed by Home, et al., J. Am. Chem. Soc. (1990) 112:2435–2437. Use of N4,N4-ethanocytosine as an alkylating agent to crosslink to single-stranded oligonucleotides has also been described by Webb and Matteucci, J. Am. Chem. Soc. (1986) 108:2764–2765; Nucleic Acids Res (1986) 14:7661–7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

In another aspect, the invention relates to an isolated protein comprising a member selected from the group consisting of:
  (a) a polypeptide comprising at least 25 contiguous amino acids of SEQ ID NO: 2, 8, 10, 12, 14, 16,18, 20, or 22;
  (b) a polypeptide which is a plant HAP3-type CCATT-box binding transcriptional activator that regulates gene expression during embryo development and maturation;
  (c) a polypeptide comprising at least 60% sequence identity to SEQ ID NO: 2, 12, 14, 16, 20, or 22, or 70% sequence identity to SEQ ID NO: 8, 10, or 18, wherein the % sequence identity is based on the entire sequence and is determined by GAP analysis using Gap Weight of 12 and Length Weight of 4;
  (d) a polypeptide encoded by a nucleic acid of claim 1;
  (e) a polypeptide encoded by a nucleic acid of SEQ ID NO: 1, 7, 9, 11, 13, 15, 17, 19, or 21; and
  (f) a polypeptide having the sequence set forth in SEQ ID NO: 2, 8, 10, 12, 14, 16, 18, 20, or 22.

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) Proc. Natl. Acad. Sci. USA 82:488–492; Kunkel et al. (1987) Methods Enzymol. 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein. In particular, it may be desirable to diminish the activity of the LEC1 gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes, including bacterial hosts such as *Eschericia coli, Salmonella typhimurium*, and *Serratia marcescens*. Eukaryotic hosts such as yeast or filamentous fungi may also be used in this invention. Since these hosts are also microorganisms, it will be essential to ensure that plant promoters which do not cause expression of the polypeptide in bacteria are used in the vector.

Commonly used prokaryotic control sequences include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva, et al., Gene 22:229–235 (1983); Mosbach, et al., Nature 302:543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastors*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A.*; Merrifield, et al., J. Am. Chem. Soc. 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein. It has been observed that high levels of LEC1 prevent germination. See Lotan et al., Cell 1998 Jun. 26; 93(7):1195–1205. Thus, temporal regulation of LEC1 expression may be desirable in certain species to permit proper germination, vegetative growth, flowering and reproduction.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration or composition is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots or dicots, preferably maize, soybeans, sunflower, sorghum, canola, wheat, alfalfa, rice, barley and millet.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, Nature 256:495–497 (1975).

Other suitable techniques involve selection of libraries of recombinant antibodies in phage or similar vectors (see, e.g., Huse et al., Science 246:1275–1281 (1989); and Ward et al., Nature 341:544–546 (1989); and Vaughan et al., Nature Biotechnology, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech., 14:845–851 (1996). Also, recombinant immunoglobulins may be produced. See, Cabilly, U.S. Pat. No. 4,816,567; and Queen et al., Proc. Natl. Acad. Sci. 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein, can be used to construct an expression cassette which can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., Ann. Rev. Genet. 22:421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., Embo J. 3:2717–2722 (1984). Electroporation techniques are described in Fromm et al., Proc. Natl. Acad. Sci. 82:5824 (1985). Ballistic transformation techniques are described in Klein et al., Nature 327:70–73 (1987).

*Agrobacterium tumefaciens*-meditated transformation techniques are well described in the scientific literature. See, for example Horsch et al., Science 233:496–498 (1984), and Fraley et al., Proc. Natl. Acad. Sci. 80:4803 (1983). For instance, *Agrobacterium* transformation of maize is described in WO 98/32326. *Agrobacterium* transformation of soybean is described in U.S. Pat. No. 5,563,055.

Other methods of transfection or transformation include (1) *Agrobacterium rhizogenes*-mediated transformation (see, e.g., Lichtenstein and Fuller In: Genetic Engineering, Vol. 6, P W J Rigby, Ed., London, Academic Press, 1987; and Lichtenstein, C. P., and Draper, J., In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, (1984)), (3) the vortexing method (see, e.g., Kindle, Proc. Natl. Acad. Sci. USA 87:1228, (1990)).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding polynucleotides can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Altering the Culture Medium to Suppress Somatic Embryogenesis in Non-Transformed Plant Cells and/or Tissues to Provide for a Positive Section Means of Transformed Plant Cells Using the following methods for controlling somatic embryogenesis, it is possible to alter plant tissue culture media components to suppress somatic embryogenesis in a plant species of interest (often having multiple components that potentially could be adjusted to impart this effect). Such conditions would not impart a negative or toxic in vitro environment for wild-type tissue, but instead would simply not produce a somatic embryogenic growth form. Introducing a transgene such as LEC1 will stimulate somatic embryogenesis and growth in the transformed cells or tissue, providing a clear differential growth screen useful for identifying transformants.

Altering a wide variety of media components can modulate somatic embryogenesis (either stimulating or suppressing embryogenesis depending on the species and particular media component). Examples of media components which, when altered, can stimulate or suppress somatic embryogenesis include;

1) the basal medium itself (macronutrient, micronutrients and vitamins; see T. A. Thorpe, 1981 for review, "Plant Tissue Culture: Methods and Applications in Agriculture", Academic Press, NY),
2) plant phytohormones such as auxins (indole acetic acid, indole butyric acid, 2,4-dichlorophenoxyacetic acid, naphthaleneacetic acid, picloram, dicamba and other functional analogues), cytokinins (zeatin, kinetin, benzyl amino purine, 2-isopentyl adenine and functionally-related compounds) abscisic acid, adenine, and gibberellic acid,
3) and other compounds that exert "growth regulator" effects such as coconut water, casein hydrolysate, and proline, and
4) the type and concentration of gelling agent, pH and sucrose concentration.

Changes in the individual components listed above (or in some cases combinations of components) have been demonstrated in the literature to modulate in vitro somatic embryogenesis across a wide range of dicotyledonous and monocotyledonous species. For a compilation of examples, see E. F. George et al. 1987. Plant Tissue Culture Media. Vol. 1: Formulations and Uses. Exergetics, Ltd., Publ., Edington, England.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., The Plant Cell, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by *Agrobacterium* can be achieved as described by Horsch et al., Science, 227:1229–1231 (1985) and Fraley et al., Proc. Natl. Acad. Sci. U.S.A. 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., Ann. Rev. of Plant Phys. 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wisc. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants which can be used in the method of the invention include monocotyledonous and dicotyledonous plants. Preferred plants include maize, wheat, rice, barley, oats, *sorghum,* millet, rye, soybean, sunflower, alfalfa, canola and cotton.

Seeds derived from plants regenerated from transformed plant cells, plant parts or plant tissues, or progeny derived from the regenerated transformed plants, may be used directly as feed or food, or further processing may occur.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Library Construction Used for the Maize LEC1 EST's

A. Total RNA Isolation

Total RNA was isolated from maize embryo and regenerating callus tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. Anal. Biochem. 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

B. Poly(A)+ RNA Isolation

The selection of poly(A)+ RNA from total RNA was performed using PolyATact system (Promega Corporation. Madison, Wis). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

C. cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

Example 2

Sequencing and cDNA Subtraction Procedures Used for Maize LEC1 EST's

A. Sequencing Template Preparation

Individual colonies were picked and DNA was prepared either by PCR with M13 forward primers and M13 reverse primers, or by plasmid isolation. All the cDNA clones were sequenced using M13 reverse primers.

B. Q-Bot Subtraction Procedure cDNA libraries subjected to the subtraction procedure were plated out on 22×22 cm² agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:
1. First strand cDNA from the same tissue from which the library was made to remove the most redundant clones.
2. 48–192 most redundant cDNA clones from the same library based on previous sequencing data.
3. 192 most redundant cDNA clones in the entire corn sequence database.
4. A Sal-A20 oligo nucleotide removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

Example 3

Identification of Maize LEC1 EST's from a Computer Homology Search

Gene identities were determined by conducting BLAST (Basic Local Alignment Search Tool; Altschul, S. F., et al., (1993) J. Mol. Biol. 215:403–410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. (1993) Nature Genetics 3:266–272) provided by the NCBI. In some cases, the sequencing data from two or more clones containing overlapping segments of DNA were used to construct contiguous DNA sequences.

Example 4

Composition of cDNA Libraries Used to Isolate and Sequence Additional cDNA Clones cDNA libraries representing mRNAs from various corn, poppy, soybean and *Vernonia* tissues were prepared (see Table 1). The characteristics of the libraries are described below.

TABLE 1

| cDNA Libraries from Corn, Poppy, Soybean and *Vernonia* Tissue |
|---|
| Corn endosperm 20 days After pollination* |
| Prickly poppy developing seeds |
| Soybean embryo, 6 to 10 days after flowering |
| Soybean embryo, 13 days after flowering |
| Soybean embryogenic suspension 2 weeks after subculture |
| Soybean mature embryo 8 weeks after subculture |
| Soybean embryogenic suspension |
| *Vernonia* developing seed* |

*These libraries were normalized essentially as described in U.S. Pat. No. 5,482,845, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) Science 252:1651). The resulting ESTs were analyzed using a Perkin Elmer Model 377 fluorescent sequencer.

Example 5

Identification of cDNA Clones Obtained from Tissue Described in Table 1

ESTs encoding plant transcription factors were identified by conducting BLAST (Basic Local Alignment Search Tool; Altschul, S. F., et al., (1993) J. Mol. Biol. 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) Nucleic Acids Res. 25:3389–3402) provided by the NCBI.

Example 6

Identification of Protein Motifs Diagnostic for LEC1 Genes

To determine the structural requirements for a LEC1 gene, HAP3 homologs were identified in our EST database and aligned. By analyzing sequence homology amongst the plant HAP3 family of transcriptional activators these sequences were observed to fall into a least two distinctive groups. All of the HAP3 sequences derived from seed or embryo specific libraries form a distinctive LEC1 group that suggests a common evolutionary origin (confirmed by phylo-dentrograms). For example within the "B domain" of all plant LEC1 sequences examined, a highly conserved CCAAT-box binding motif has been found to contain the non-variable residues methionine, proline, isoleucine, alanine, asparagine, valine, and isoleucine (MPIANVI). LEC1 genes are highly divergent outside of the region spanning the DNA binding and subunit interaction motifs. The low levels of homology between these genes make it difficult to identify these based solely on a hybridization strategy. Using sequences from maize, soybean, wheat, prickly poppy, *Vernonia*, and *Arabidopsis* a motif diagnostic for LEC1 genes was identified, the specific amino acid substitutions for these species was clarified and the positions at which amino acid substitutions occur within the LEC1 group was determined (SEQ ID NO: 23). Using Blast, the motif in SEQ ID NO: 23 was used to correctly distinguish LEC1's from other closely related plant HAP3 transcriptional activators.

Example 7

Transformation and Regeneration of Maize Callus

Immature maize embryos from greenhouse or field grown High type II donor plants were bombarded with a plasmid containing a polynucleotide of the invention (LEC1). The LEC1 polynucleotide was operably linked to a constitutive promoter such as nos, or an inducible promoter, such as In2, plus a plasmid containing the selectable marker gene PAT (Wohlleben et al. (1988) *Gene* 70:25–37) that confers resistance to the herbicide Bialaphos fused to the Green Fluorescence protein. Transformation was performed as follows.

The ears were surface sterilized in 50% Chlorox bleach plus 0.5% Micro detergent for 20 minutes, and rinsed two times with sterile water. The immature embryos were excised and placed embryo axis side down (scutellum side up), 25 embryos per plate. These were cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos were transferred to 560 Y medium for 4 hours and were arranged within the 2.5-cm target zone. Medium 560Y is a high osmoticum medium (560L with high sucrose concentration).

A plasmid vector comprising a polynucleotide of the invention operably linked to the selected promoter was constructed. This plasmid DNA plus plasmid DNA containing a PAT selectable marker was precipitated onto 1.1 µm (average diameter) tungsten pellets using a $CaCl_2$ precipitation procedure as follows: 100 µl prepared tungsten particles (0.6 mg) in water, 20 µl (2 µg) DNA in TrisEDTA buffer (1 µg total), 100 µg 2.5 M $CaCl_2$, 40 µl 0.1 M spermidine.

Each reagent was added sequentially to the tungsten particle suspension. The final mixture was sonicated briefly. After the precipitation period, the tubes were centrifuged briefly, liquid removed, washed with 500 ml 100% ethanol, and centrifuged again for 30 seconds. Again the liquid was removed, and 60 µl 100% ethanol was added to the final tungsten particle pellet. For particle gun bombardment, the tungsten/DNA particles were briefly sonicated and 5 µl spotted onto the center of each macrocarrier and allowed to dry about 2 minutes before bombardment.

The sample plates were bombarded at a distance of 8 cm from the stopping screen to the tissue, using a Dupont biolistics helium particle gun. All samples received a single shot at 650 PSI, with a total of ten aliquots taken from each tube of prepared particles/DNA.

Four to 12 hours post bombardment, the embryos were moved to 560P (a low osmoticum callus initiation medium similar to 560L but with lower silver nitrate), for 3–7 days, then transferred to 560R selection medium, an N6 based medium similar to 560P containing 3 mg/liter Bialaphos, and subcultured every 2 weeks. Multicellular GFP cell clusters became visible after two weeks and their numbers were periodically recorded. After approximately 10 weeks of selection, selection-resistant GFP positive callus clones were sampled for PCR and activity of the polynucleotide of interest. Positive lines were transferred to 288J medium, an MS-based medium with lower sucrose and hormone levels, to initiate plant regeneration. Following somatic embryo maturation (2–4 weeks), well-developed somatic embryos were transferred to medium for germination and transferred to the lighted culture room. Approximately 7–10 days later, developing plantlets were transferred to medium in tubes for 7–10 days until plantlets were well established. Plants were then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Plants are monitored for expression of the polynucleotide of interest.

Example 8

Ectopic Expression of Maize LEC1 to Induce Somatic Embryogenesis

Using the genotype High type II as an example, embryos were isolated and cultured on 560L medium for 3–5 days. Four to twelve hours before bombardment these embryos were transferred to high osmotic 560Y medium. Expression cassettes containing the LEC1 cDNA were then co-introduced into the scutella of these embryos along with an expression cassette containing the Pat gene fused to the Green Fluorescent protein using methods described in Example 7. Embryos from a single ear were divided evenly between treatments. Four to 12 hours following bombardment embryos were then transferred back to a low osmoticum callus initiation medium (560P) and incubated in the dark at 26° C. After 3–7 days of culture these embryos were moved to 560R selection medium. Cultures were then transferred every two weeks until transformed colonies appear. Cultures were also examined microscopically for GFP expression. LEC1 expression was expected to stimulate adventive embryo formation. This was apparent when the cultures were compared to controls (transformed without the LEC1 cDNA or non-induced).

A. Ectopic Expression of the Maize LEC1 Polynucleotide in Tobacco is Sufficient to Induce Somatic Embryogenesis in Tobacco Leaves A maize LEC1 polynucleotide was placed into an agrobacterium expression cassette driven by the maize safener-induced In2 promoter (this promoter is leaky and expresses at low levels without induction). Also between the left and right T-DNA borders was the bar gene driven by 35S promoter and the Green Fluorescence Protein driven by the ubiquitin promoter. A similar construct was made without the LEC1 polynucleotide to be used as a control. Tobacco leaf discs from variety SR1 were co-cultured with *Agrobacterium* as described by Horsch et al. (1985, Science 227: 1229–1231) except selecting with bialaphos rather than kanamycin. Transformants were selected on medium containing 3 mg/l bialaphos. Of the numerous transformed shoot obtained, ectopic embryos were visible on the leaves of a single LEC1 transformant. None were visible on control plants. Although the frequency was low, ectopic somatic embryo formation was also reported to be a rare event in *Arabidopsis* LEC1 transformants (Lotan et al. 1998).

B. Transformation Frequency was Improved by LEC1 Introduced Using Particle-Mediated DNA Delivery.

A series of expression cassettes were made to evaluate the effects of LEC1 expression on maize transformation. The maize LEC1 polynucleotide was placed under the control of the In2 promoter (weakly induced with the auxin levels used under normal culture conditions and strongly-induced with safener), the barley NUC1 promoter (expressed strongly in the nucellus), the Ubiquitin promoter (strongly expressed constitutively), and the nos promoter (weakly expressed constitutively). A frame-shift version of the In2:LEC1 cassette was made along with an In2:ZM-NF-YB (designated as In2:HAP3 henceforth) construct (The maize ZM NF-YB is non-LEC1 type of HAP3 transcriptional activator (Li et al Nucleic Acids Res. 20:1087–1091) for use as negative controls. All of these constructs were co-bombarded with the Pat~GFP fusion construct (designated as PAT~GFP) into high type II embryos as described in Example 7. Also, as in Example 7, immature embryos were harvested from separate ears, and the embryos from each ear were divided equally between treatments to account for ear-to-ear variability (for example, in an experiment comparing a control plasmid with this same plasmid+LEC1, one-half the total embryos from each ear would be used for each treatment. In some cases the control treatment contained the Pat~GFP construct co-bombarded with GUS. Transformation frequency was determined by counting the numbers of embryos with large multicellular GFP-positive cells clusters using a GFP microscope, and representing these as a percentage of the original number of embryos bombarded. No distinction was made between embryos with single or multiple events. In all cases, the functional LEC1 expression cassettes increased transformation frequencies over the control treatment (the LEC1 expression cassette also increased the incidence of multiple, i.e. 2–3, multicellular transgenic clones growing from the same immature embryo, but as stated above we only scored these as a single event, and are providing a conservative representation of LEC1's ability to improve transformation). For example, transformation frequencies in control treatments for three consecutive experiments were 5.1, 7.4 and 0.8%. In balanced side-by-side comparisons for the same three experiments, transformation frequencies with the LEC1 polynucleotide (In2::LEC1::pinII) were 28.8, 25.7 and 12.4%, respectively. In addition to increasing the absolute number of transformants recovered from a given amount of target tissue, LEC1 transformants appeared earlier than the control transformants (suggesting that the LEC1 polynucleotide also stimulated growth rates).

As a more stringent control, an expression vector was constructed in which a LEC1 gene, frame-shifted immediately after the start codon, was placed behind the In2 promoter. In this experiment using embryos from 3 separate ears, the transformation frequencies in the control (frame-shifted LEC1) treatments were 2.7, 6.0 and 2.0%, while the transformation frequencies for the LEC1 treatments were 62.7, 26 and 42.7%. This demonstrated clearly that expression of the in-frame LEC1 polynucleotide was associated with dramatic increases in transformation efficiency.

Increasing the promoter strength (driving LEC1 expression) increased transformation frequencies. For example, an experiment was performed to compare the In2, nos and UBI promoters. Based on our experience with these two promoters driving other genes, the In2 promoter (in the absence of an inducer other than auxin from the medium) would drive expression at very low levels. The nos promoter has been shown to drive moderately-low levels of transgene expression (approximately 10- to 30-fold lower than the maize ubiquitin promoter, but still stronger than In2 under the culture conditions used in this experiment). Two control treatments were used in this experiment; the frame-shifted LEC1 driven by the In2 promoter, or a maize In2:HAP3 polynucleotide (a "non-LEC1 type" representative of the transcriptional factor family to which LEC1 belongs). Both control treatments resulted in low transformation frequencies. After 3 weeks, the transformation frequency for the In2:frame-shift-LEC1 (FS) treatment was 4.8%, while for the In2:HAP3 treatment it was 2%. The In2:LEC1, nos:LEC1 and UBI:LEC1 treatments resulted in 14%, 28% and 30% transformation frequencies, respectively. Within these treatments there was also an increase in the overall frequency of large, rapidly growing calli. For the control treatments, the frequencies of large, vigorous GFP+ calli (relative to the starting number of embryos) was low (1.6 and 0% for the frame-shift or In2:HAP3, respectively). For the In2, nos and UBI treatments the overall frequencies of large, vigorous calli was 4, 13.3 and 20%, respectively. This is consistent with the interpretation that increased LEC1 expression resulted in more rapid in vitro growth of transgenic tissue. As is typical for transformation experiments scored in this fashion, between 3–6 weeks the number of recovered transformants continues to rise. After 5 weeks (post-bombardment), the frequency of healthy, growing transformants was 4.8 and 7.3% for the FS and HAP3 controls, while for the In2, nos and UBI-driven LEC1 treatments the frequencies were 22, 29.3 and 35.3%.

C. Transformation Frequency was Improved by LEC1 Introduced Using *Agrobacterium*.

The *Agrobacterium* strains containing the superbinary plasmids described in Example 8A were used to transformed High type II embryos. Briefly, colonies containing the engineered *Agrobacterium* were grown to log phase in minimal A medium. Log phase cells were collected by centrifugation and resuspended in 561Q medium (N6 salts, Eriksson's vitamins, 1.5 mg/l 2,4-D, 68.5 g/l sucrose, 36 g/l glucose, plus 20 mg/l acetosyringone). Immature embryos, 1.5–2 mm in length, were excised and immersed in this solution at a concentration of $5 \times 10^8$ bacterial cells/ml. Embryos were vortexed in this medium and allowed to sit for 5 minutes. The embryos were then removed and placed on 562P medium (560P medium with 100 mM acetosyringone and incubated at 20° C. for 3 days. Embryos were moved again to 563N medium (an agar solidified medium similar to 560P with 100 mg/l carbenicillin, 0.5 g/l MES and reduced 2,4-D) and cultured at 28° C. for 3 days. Embryos were then moved to 563O medium (563N medium with 3 mg/l bialaphos) and transferred thereafter every 14 days to fresh 563O medium.

Bialaphos resistant GFP+colonies were counted using a GFP microscope and transformation frequencies were determined as described in example 8B. Similar to particle gun experiments, transformation frequencies were greatly increased in the LEC1 treatment. For example, transformation frequencies for the control treatment across embryos taken from 7 separate ears were 7.1, 40.9, 11.1, 7.4, 11.5, 12, 30.8, and 16.6%. The side-by-side comparison for the LEC treatment (in the same order of ears as above) showed that transformation frequencies were 13.5, 47, 55.8, 37.1, 40.6, 30, 57.1 and 40.8%. Averaged across all 7 ears, the average transformation frequency for the control was 16.6% while that of the LEC1 treatment was 40.8%. This represents a substantial increase for an already high baseline produced by *Agrobacterium*-mediated transformation. Comparing across ears, it was observed that the beneficial effects on transformation frequency were the greatest when the control frequencies were low.

D. Transformants were Recovered Using LEC1 Expression under Reduced Auxin Levels or in the Absence of Auxins in the Medium, and in the Absence of Herbicide or Antibiotic Selection.

To determine if LEC1 could be used in a positive selection scheme, particle gun transformation experiments were initiated as described in Example 4 and transformants were selected on medium with normal auxin levels, or on medium with reduced or no auxin, or visually (using GFP) on medium without bialaphos. Transformation frequencies were based on the numbers of embryos with one or more multicellular GFP positive cell clusters. In the first experiment to test this concept, there were two treatment variables. The first was that immature embryos were bombarded with the control plasmid (UBI:PAT~GFP) or with UBI: PAT~GFP+In2:LEC1. The second variable was that the bombarded embryos were divided onto either normal bialaphos-containing selection medium (with normal auxin levels of 2 mg/l 2,4-D), or medium with no bialaphos and reduced 2,4-D levels (0.5 mg/l). As expected from previous results, on bialaphos selection the LEC1 treatment resulted in a higher transformation frequency than the control (5.7 versus 2.5%). It was also anticipated that the low auxin medium (0.5 mg/l 2,4-D) would result in reduced growth rates. Consistent with this, for the control plasmid treatment (UBI:PAT~GFP), recovery of GFP-expressing (fluorescent) colonies was reduced relative to highly-effective bialaphos-selection treatment, dropping down to 0.6%. In contrast, it appeared that LEC1 expression, through its stimulation of embryogenesis, may have compensated for the low auxin environment, providing a growth advantage to the transgenic colonies, and maintaining the efficiency of transformant recovery at 4.0% (still in the same range as the LEC1/bialaphos-selected treatment). It's clear from this result that the inclusion of LEC1 improved colony growth on reduced auxin relative to the control.

On medium completely devoid of auxin, colonies were only observed in the LEC1 treatment. In this experiment, immature embryos were bombarded with either the control plasmid (UBI:PAT~GFP) or with UBI:PAT~GFP+In2: LEC1, and then plated either onto 3.0 mg/l bialaphos, 2.0 mg/l 2,4-D medium or onto no-bialaphos, no 2,4-D medium (in this latter treatment, wild-type maize callus will not exhibit embryogenic growth). Again, as expected, the LEC1 polynucleotide increased transformation to 22.7% over the control plasmid value of 8% on normal auxin-containing, bialaphos selection medium. Also, as expected, no transformants were recovered with the control plasmid on medium devoid of exogenous auxin. Surprisingly, in the LEC1 treated embryos transformants were recovered at a 4% frequency (this was still higher than the control plasmid on bialaphos selection).

Even on auxin-containing medium, the LEC1 polynucleotide in combination with GFP+ expression can be used to recover transformants without chemical selection. For example, under these conditions the recovery of transformants was relatively efficient (16% compared to 18% for bialaphos selection), but this required more diligence than the low- or no-auxin treatments above to separate the GFP-expressing colonies from the growing callus population.

E. LEC1 Improves the Embryogenic Phenotype and Regeneration Capacity of Inbreds.

Immature embryos from the inbred PHP38 were isolated, cultured and transformed as described in example 4 with the following changes. Embryos were initially cultured on 601H medium (a MS based medium with 0.1 mg/l zeatin, 2 mg/l 2,4-D, MS and SH vitamins, proline, silver nitrate, extra potassium nitrate, casein hydrolysate, gelrite, 10 g/l glucose and 20 g/l sucrose). Prior to bombardment embryos were moved to a high osmoticum medium (modified Duncan's with 2 mg/l 2,4-D and 12% sucrose). Post bombardment, embryos were moved to 601H medium with 3 mg/l bialaphos for two weeks. Embryos were then moved to 601H medium without proline and casein hydrolysate with 3 mg/l bialaphos and transferred every two weeks. Transformation frequency was determined by counting the numbers of bialaphos resistant GFP-positive colonies. Colonies were also scored on whether they had an embryogenic (regenerable) or non-embryogenic phenotype. In PHP38, the LEC1 polynucleotide increased transformation frequency and improved the regenerative potential of the callus. For example, a balanced experiment (the embryos from each harvested ear were divided equally between treatments) was conducted in which PHP38 immature embryos were bombarded with the control plasmid (UBI::PAT~GFP::pinII) in one treatment, with the UBI::PAT~GFP::pinII plasmid+In2:: LEC1, or with the UBI::PAT~GFP::pinII plasmid+nuc1:: LEC1 (a maize nucellus-specific promoter driving LEC1 expression). The frequency of GFP+ calli growing on bialaphos-containing media (relative to the starting number of embryos) was determined 6 weeks after bombardment. For the control treatment, the transformation frequency was 1.2%, while for the In2:LEC1 and nuc1::LEC1 treatments the transformation frequencies were 3.2 and 2.0% respectively. In addition, the presence of the LEC1 polynucleotide appeared to greatly improve the regeneration capacity of the recovered transformants. None of the control transformants (UBI::PAT~GFP::pinII alone) had an embryogenic, regenerable phenotype, while the transformants recovered from the In2:LEC1 and nuc1::LEC1 treatments all exhibited a more vigorous, embryogenic growth pattern. This has been born out in the ability to recover plants. Callus from the In2:LEC1 and nuc1::LEC1 treatments has produced many healthy plants.

Example 9

Transient Expression of the LEC1 Polynucleotide Product to Induce Somatic Embryogenesis It may be desirable to "kick start" somatic embryogenesis by transiently expressing the LEC-1 polynucleotide product. This can be done by delivering LEC1 5'capped polyadenylated RNA, expression cassettes containing LEC-1 DNA, or LEC-1 protein. All of these molecules can be delivered using a biolistics particle gun. For example 5'capped polyadenylated LEC1 RNA can easily be made in vitro using Ambion's mMessage mMachine kit. Following the procedure outline above RNA is co-delivered along with DNA containing an agronomically useful expression cassette. The cells receiving the RNA will immediately form somatic embryos and a large portion of these will have integrated the agronomic gene. Plants regenerated from these embryos can then be screened for the presence of the agronomic gene.

Example 10

Use of the Maize LEC1 to Induce Apomixis

Maize expression cassettes directing LEC1 expression to the inner integument or nucellus can easily be constructed. An expression cassette directing expression of the LEC1 polynucleotide to the nucellus was made using the barley Nuc1 promoter. Embryos were co-bombarded with the selectable marker PAT fused to the GFP gene along with the nucellus specific LEC1 expression cassette described above. Both inbred (PHP38) and GS3 transformants were obtained and regenerated as described in examples 4 and 5. Transformation frequencies were also increased over the control using the nuc1:LEC1 polynucleotide (see Example 8 above).

It is anticipated that the regenerated plants will then be capable of producing de novo embryos from LEC1 expressing nucellar cells. This is complemented by pollinating the ears to promote normal central cell fertilization and endosperm development. In another variation of this scheme, nuc1:LEC1 transformations could be done using a FIE-null genetic background which would promote both de novo embryo development and endosperm development without fertilization (see Ohad et al. 1999 The Plant Cell 11:407–415; also pending U.S. application Ser. No. 60/151575 filed Aug. 31, 1999). Upon microscopic examination of the developing embryos it will be apparent that apomixis has occurred by the presence of embryos budding off the nucellus. In yet another variation of this scheme the LEC1 polynucleotide could be delivered as described above into a homozygous zygotic-embryo-lethal genotype. Only the adventive embryos produced from somatic nucellus tissue would develop in the seed.

Example 11

Expression of Chimeric Genes in Microbial Cells

The cDNAs encoding the instant transcription factors can be inserted into the T7 E. coli expression vector pBT430. This vector is a derivative of pET-3a (Rosenberg et al (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the polynucleotide encoding the transcription factor are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 hours at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 12

Evaluating Compounds for their Ability to Inhibit the Activity of Plant Transcription Factors The transcription factors described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant transcription factors may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant transcription factors, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the transcription factors are expressed as fusion proteins, the purification protocol may include the use of an affinity resin which is specific for the fusion protein tag attached to the expressed enzyme or an affinity resin containing ligands which are specific for the enzyme. For example, a transcription factor may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activity of the transcription factors disclosed herein. Assays may be conducted under well-known experimental conditions that permit optimal enzymatic activity.

Example 13

LEC1 Expression Resulted in Increased Growth Rates, which could be Used as a Screening Criterion for Positive Selection of Transformants Using two promoters of increasing strength to drive LEC1 expression in maize, it appeared that LEC1 stimulated callus growth over control treatments and the stronger promoter driving LEC1 resulted in faster growth than with the low-level promoter. For example, an experiment was performed to compare the In2 and nos promoters. As noted above, based on our experience with these two promoters driving other genes, the In2 promoter (in the absence of an inducer other than auxin from the medium) would drive expression at very low levels. The nos promoter has been shown to drive moderately-low levels of transgene expression (approximately 10- to 30-fold lower than the maize ubiquitin promoter, but still stronger than In2 under the culture conditions used in this experiment). One control treatment was used in this experiment, the UBI:PAT~GFPmo:pinII construct by itself (with no LEC1). Hi-II immature embryos were bombarded as previously described, and transgenic, growing events were scored at 3 and 6 weeks. The control treatment resulted in a transformation frequency of 0.8%. The In2:LEC1 and nos:LEC1 treatments resulted in transformation frequencies of 26.5 and 40.7%, respectively.

Within these treatments there was also an increase in the overall frequency of large, rapidly growing calli, relative to the control treatment. For this data, the fresh weight of transformed calli were recorded 2 months after bombardment. Assuming that all the transgenic events started as single transformed cells within a few days after bombardment, these weights represent the relative growth rate of these transformants during this period (all tissue was subcultured and weighed for each transformant; mean weights and standard deviations were calculated for each treatment). For the control treatment, the mean transformant weight after two months was 37+/−15 mg (n=6). For the In2:LEC1 and nos:LEC1 treatments, the mean transformant weights were 126+/−106 and 441+/−430 mg, respectively. If the control treatment was set at a relative growth value of 1.0, this means that transformants in the In2:LEC1 and nos:LEC1 treatments grew 3.4 and 12-fold faster than the control. From this data, it appears that increasing LEC1 expression resulted in a concomitant increase in callus growth rate.

Example 14

The Use of LEC1 Polynucleotide as a Positive Selection System for Wheat Transformation and for Improving the Regeneration Capacity of Wheat Tissues Method Plant Material Seeds of wheat Hybrinova lines NH535 and BO 014 were sown into soil in plug trays for vernalisation at 6° C. for eight weeks. Vernalized seedlings were transferred in 8" pots and grown in a controlled environment room. The growth conditions used were; 1) soil composition: 75% L&P fine-grade peat, 12% screened sterilized loam, 10% 6 mm screened, lime-free grit, 3% medium grade vermiculite, 3.5 kg Osmocote per m$^3$ soil (slow-release fertiliser, 15-11-13 NPK plus micronutrients), 0.5 kg PG mix per m$^3$ (14-16-18 NPK granular fertiliser plus micronutrients, 2) 16 h photoperiod (400 W sodium lamps providing irradiance of ca. 750 µE s$^{-1}$ m$^{-2}$), 18 to 20° C. day and 14 to 16° C. night temperature, 50 to 70% relative air humidity and 3) pest control: sulphur spray every 4 to 6 weeks and biological control of thrips using *Amblyseius caliginosus* (Novartis BCM Ltd, UK).

Isolation of Explants and Culture Initiation

Two sources of primary explants were used; scutellar and inflorescence tissues. For scutella, early-medium milk stage grains containing immature translucent embryos were harvested and surface-sterilized in 70% ethanol for 5 min and 0.5% hypochlorite solution for 15–30 min. For inflorescences, tillers containing 0.5–1.0 cm inflorescences were harvested by cutting below the inflorescence-bearing node (the second node of a tiller). The tillers were trimmed to approximately 8–10 cm length and surface-sterilized as above with the upper end sealed with Nescofilm (Bando Chemical Ind. Ltd, Japan).

Under aseptic conditions, embryos of approximately 0.5–1.0 mm length were isolated and the embryo axis removed. Inflorescences were dissected from the tillers and cut into approximately 1 mm pieces. Thirty scutella or 1 mm inflorescence explants were placed in the center (18 mm target circle) of a 90 mm Petri dish containing MD0.5 or L7D2 culture medium. Embryos were placed with the embryo-axis side in contact with the medium exposing the scutellum to bombardment whereas inflorescence pieces were placed randomly. Cultures were incubated at 25±° C. in darkness for approximately 24 h before bombardment. After bombardment, explants from each bombarded plate were spread across three plates for callus induction.

Culture Media

The standard callus induction medium for scutellar tissues (MD0.5) consisted of solidified (0.5% Agargel, Sigma A3301) modified MS medium supplemented with 9% sucrose, 10 mg $l^{-1}$ AgNO$_3$ and 0.5 mg $l^{-1}$ 2,4-D (Rasco-Gaunt et al., 1999). Inflorescence tissues were cultured on L7D2 which consisted of solidified (0.5% Agargel) L3 medium supplemented with 9% maltose and 2 mg $l^{-1}$ 2,4-D (Rasco-Gaunt and Barcelo, 1999). The basal shoot induction medium, RZ contained L salts, vitamins and inositol, 3% w/v maltose, 0.1 mg $l^{-1}$ 2,4-D and 5 mg $l^{-1}$ zeatin (Rasco-Gaunt and Barcelo, 1999). Regenerated plantlets were maintained in RO medium with the same composition as RZ, but without 2,4-D and zeatin.

DNA Precipitation Procedure and Particle Bombardment

Submicron gold particles (0.6 μm Micron Gold, Bio-Rad) were coated with a plasmid containing the maize In-2:LEC1 construct following the protocol modified from the original Bio-Rad procedure (Barcelo and Lazzeri, 1995). The standard precipitation mixture consisted of 1 mg of gold particles in 50 μl SDW, 50 μl of 2.5 M calcium chloride, 20 μl of 100 mM spermidine free base and 5 μl DNA (concentration 1 μg μl$^{-1}$). After combining the components, the mixture was vortexed and the supernatant discarded. The particles were then washed with 150 μl absolute ethanol and finally resuspended in 85 μl absolute ethanol. The DNA/gold ethanol solution was kept on ice to minimise ethanol evaporation. For each bombardment, 5 μl of DNA/gold ethanol solution (ca. 60 μg gold) was loaded onto the macrocarrier.

Particle bombardments were carried out using DuPont PDS 1000/He gun with a target distance of 5.5 cm from the stopping plate at 650 psi acceleration pressure and 28 in. Hg chamber vacuum pressure.

Regeneration of Transformants

For callus induction, bombarded explants were distributed over the surface of the medium in the original dish and two other dishes and cultured at 25±1° C. in darkness for three weeks. Development of somatic embryos from each callus were periodically recorded. For shoot induction, calluses were transferred to RZ medium and cultured under 12 h light (250 μE s$^{-1}$ m$^{-1}$, from cool white fluorescent tubes) at 25±1° C. for three weeks for two rounds. All plants regenerating from the same callus were noted. Plants growing more vigorously than the control cultures were potted in soil after 6–9 weeks in R0 medium. The plantlets were acclimatized in a propagator for 1–2 weeks. Thereafter, the plants were grown to maturity under growth conditions described above.

DNA Isolation from Callus and Leaf Tissues

Genomic DNA was extracted from calluses or leaves using a modification of the CTAB (cetyltriethylammonium bromide, Sigma H5882) method described by Stacey and Isaac (1994). Approximately 100–200 mg of frozen tissues was ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples were allowed to cool at room temperature for 15 min before a single protein extraction with approximately 1 ml 24:1 v/v chloroform: octanol was done. Samples were centrifuged for 7 min at 13,000 rpm and the upper layer of supernatant collected using wide-mouthed pipette tips. DNA was precipitated from the supernatant by incubation in 95% ethanol on ice for 1 h. DNA threads were spooled onto a glass hook, washed in 75% ethanol containing 0.2 M sodium acetate for 10 min, air-dried for 5 min and resuspended in TE buffer. Five μl RNAse A was added to the samples and incubated at 37° C. for 1 h.

For quantification of genomic DNA, gel electrophoresis was performed using an 0.8% agarose gel in 1×TBE buffer. One microliter of the samples were fractionated alongside 200, 400, 600 and 800 ng μl$^{-1}$ λ uncut DNA markers.

Polymerase Chain Reaction (PCR) Analysis

The presence of the maize LEC1 polynucleotide was analyzed by PCR using 100–200 ng template DNA in a 30 ml PCR reaction mixture containing 1× concentration enzyme buffer (10 mM Tris-HCl pH 8.8, 1.5 mM magnesium chloride, 50 mM potassium chloride, 0.1% Triton X-100), 200 μM dNTPs, 0.3 μM primers and 0.022 U TaqDNA polymerase (Boehringer Mannheim). Thermocycling conditions were as follows (30 cycles): denaturation at 95° C. for 30 s, annealing at 55° C. for 1 min and extension at 72° C. for 1 min. Primer sequences (F=forward; R=reverse) were used. Approximate PCR product length was 620 bp.

Results

Following experiments to show increased regeneration capacity and improvement of maize transformation frequencies by expression of maize LEC1, the polynucleotide was then introduced into wheat scutellar and inflorescence explants, driven by the maize In2 promoter. Both tissues are used for wheat transformation.

Subsequent to the induction of somatic embryos from both tissues after three weeks on a 2,4-D-containing induction medium, calluses were assessed prior to transfer onto shoot regeneration medium. Callus assessment involved: a) scoring calluses as 0=non-embryogenic callus, 1=25%, 2=25–50%, 3=50–75%, 4=75–100% of callus surface embryogenic, and b) determining embryogenic capacity expressed in percentage as the number of embryogenic calluses/total number of calluses (scutella or inflorescence) assessed.

Scutellum Calluses

Mean callus scores of control (1.4±0.3) and LEC-bombarded (1.4±0.3) scutellar tissues of wheat line NH535 were not significantly different. However, callus score of LEC-bombarded scutella (1.5±0.5) of wheat line BO 014 was significantly improved in comparison with the control (0.5±0.2). Similarly, embryogenic capacity of line NH535 did not seem to be affected by LEC treatment (LEC calluses=84.3±9.3%, control calluses=90%). However, LEC-bombarded line BO 014 had clear increases in the embryogenic callus frequency (LEC calluses=75.4±16.8%, control calluses=36.7±4.7%). Examining the quality of embryogenic calluses formed, both lines showed significant increases in the number of 'good' calluses produced i.e. calluses with scores of 3 or 4. 'Good' quality callus of line NH535 increased from 5 to 22.3% whilst line BO 014 increased from 0 to 23.6%. These calluses were generally large, rapidly growing and vigorous.

After callus induction and assessment, calluses were transferred onto shoot induction media for a total of six weeks. Shoot regeneration of calluses was determined, as the number of shoot regenerating calluses/total number of calluses assessed (expressed as percentages). Shoot regeneration of cultures corresponded with the quality and quantity of somatic embryos produced in each callus. Hence, regeneration of LEC-bombarded (71.9±12.1) and control (70±14) callus tissues of line NH535 were not significantly different. However, regeneration of LEC-bombarded calluses (52.3±26.9) of wheat line BO 014 was significantly improved in comparison with the control (15.6±6.3).

To test the suitability of LEC as a positive selection system for wheat, sample tissues from vigorous calluses were analyzed for the presence of LEC sequences. Forty-one BO 014 and 13 NH535 calluses were selected. The results were that 10/41 BO 014 calluses and 8/13 NH535 were PCR positive. Thus, transformed lines were identified without selection at frequencies of 24.4% and 61.5%. These frequencies are comparable with conventional selection systems such as herbicide- and antibiotic-resistance systems (e.g. bar, nptII) applied in wheat transformation where selection 'escape' frequencies are commonly high and variable. Furthermore, we know of no other report of wheat transformation by morphological selection in the absence of a selection agent.

Callus transformation frequencies were 5.6% and 4.4% in NH535 and BO 014 lines, respectively. Transgenic plants were also recovered from LEC-positive callus lines. Seven non-clonal plants were recovered from NH535 and six non-clonal plants were recovered from BO 014 to give plant transformation frequencies of 3.9 and 3.3%, respectively, based on the number of explants bombarded.

Inflorescence Calluses

The use of inflorescence tissues as explants for the tissue culture and transformation of wheat offer several advantages over seed explants such as scutella (Rasco-Gaunt and Barcelo, 1999). However, responses of these tissues to culture are highly genotype-dependent and calluses are often non-regenerative despite having a 'highly-embryogenic' appearance. Hence, LEC was introduced into inflorescence tissues to see whether regeneration could be enhanced on a poorly regenerating line such BO 014.

Using line BO 014, shoot regeneration was significantly improved in LEC-bombarded tissues, although callus quality appeared similar in bombarded and control tissues. Whereas no shoot was regenerated from control cultures, eight plants were regenerated from LEC-bombarded calluses to give a shoot regeneration frequency of 10.7%.

Summary of tissue culture data

| Wheat line | Treatment | Mean callus score (0–4) | Embryo. Capacity (%) | % Good calluses (score 3 & 4) | Regeneration (%) |
|---|---|---|---|---|---|
| NH 535 | Control | 1.4 ± 0.3 | 90.0 | 5 | 70 ± 14 |
|  | LEC1 | 1.4 ± 0.3 | 84.3 ± 9.3 | 22.3 | 71.9 ± 12.1 |
| BO 014 | Control | 0.5 ± 0.2 | 36.7 ± 4.7 | 0 | 15.6 ± 6.3 |
|  | LEC1 | 1.5 ± 0.5 | 75.4 ± 16.8 | 23.6 | 52.3 ± 26.9 |

Type of callus produced per treatment per line

| Callus Score | NH535 Control | NH535 LEC1 | BO014 Control | BO014 LEC1 |
|---|---|---|---|---|
| 0 | 10 | 15.7 | 63.2 | 25 |
| 1 | 45 | 43.3 | 26.3 | 30 |
| 2 | 40 | 28.7 | 10.5 | 21.4 |
| 3 | 5 | 11.2 | 0 | 17.9 |
| 4 | 0 | 1.1 | 0 | 5.7 |

Transformation Frequency

| Wheat line | Callus line | Plant line (non-clonal) |
|---|---|---|
| NH 535 | 10/180 (5.6%) | 7/180 (3.9%) |
| BO 014 | 8/180 (4.4%) | 6/180 (3.3%) |

Example 15

Expression of Chimeric Genes in Dicot Cells

The LEC1 polynucleotide can also be used to improve the transformation of soybean. To demonstrate this the construct consisting of the In2 promoter and LEC1 coding region were introduced into embryogenic suspension cultures of soybean by particle bombardment using essentially the methods described in Parrott, W. A., L. M. Hoffman, D. F. Hildebrand, E. G. Williams, and G. B. Collins, (1989) Recovery of primary transformants of soybean, Plant Cell Rep. 7:615–617. This method with modifications is described below.

Seed was removed from pods when the cotyledons were between 3 and 5 mm in length. The seeds were sterilized in a Chlorox solution (0.5%) for 15 minutes after which time the seeds were rinsed with sterile distilled water. The immature cotyledons were excised by first cutting away the portion of the seed that contains the embryo axis. The cotyledons were then removed from the seed coat by gently pushing the distal end of the seed with the blunt end of the scalpel blade. The cotyledons were then placed (flat side up) SB1 initiation medium (MS salts, B5 vitamins, 20 mg/L 2,4-D, 31.5 g/l sucrose, 8 g/L TC Agar, pH 5.8). The Petri plates were incubated in the light (16 hr day; 75–80 µE) at 26° C. After 4 weeks of incubation the cotyledons were transferred to fresh SB1 medium. After an additional two weeks, globular stage somatic embryos that exhibit proliferative areas were excised and transferred to FN Lite liquid medium (Samoylov, V. M., D. M. Tucker, and W. A. Parrott (1998) Soybean [Glycine max (L.) Merrill] embryogenic cultures: the role of sucrose and total nitrogen content on proliferation. In Vitro Cell Dev. Biol.-Plant 34:8–13). About 10 to 12 small clusters of somatic embryos were placed in 250 ml flasks containing 35 ml of SB172 medium. The soybean embryogenic suspension cultures were maintained in 35 mL liquid media on a rotary shaker, 150 rpm, at 26° C. with florescent lights (20 µE) on a 16:8 hour day/night schedule. Cultures were sub-cultured every two weeks by inoculating approximately 35 mg of tissue into 35 mL of liquid medium.

Soybean embryogenic suspension cultures were then be transformed using particle gun bombardment (Klein et al. (1987) Nature (London) 327:70, U.S. Pat. No. 4,945,050). A BioRad Biolistic™ PDS1000/HE instrument was used for these transformations. A selectable marker gene which was used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from *E. coli*; Gritz et al. (1983) Gene 25:179–188) and the 3' region of the nopaline synthase gene from the T-DNA of the Ti plasmid of *Agrobacterium tumefaciens*.

To 50 µL of a 60 mg/mL 1 µm gold particle suspension was added (in order): 5 µm DNA (1 µg/µL), 20 µm spermidine (0.1 M), and 50 µL CaCl$_2$ (2.5 M). The particle preparation was agitated for three minutes, spun in a microfuge for 10 seconds and the supernatant removed. The DNA-coated particles were washed once in 400 µL 70% ethanol and resuspended in 40 µL of anhydrous ethanol. The DNA/particle suspension was sonicated three times for one second each. Five µL of the DNA-coated gold particles were then loaded on each macro carrier disk.

Approximately 300–400 mg of a two-week-old suspension culture was placed in an empty 60×15 mm petri dish and the residual liquid removed from the tissue with a pipette. Membrane rupture pressure was set at 1100 psi and the chamber was evacuated to a vacuum of 28 inches mercury. The tissue was placed approximately 8 cm away from the retaining screen, and was bombarded three times. Following bombardment, the tissue was divided in half and placed back into 35 ml of FN Lite medium.

Five to seven days after bombardment, the liquid medium was exchanged with fresh medium. Eleven days post bombardment the medium was exchanged with fresh medium containing 50 mg/mL hygromycin. This selective medium was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos, or tissue was regenerated into whole plants by maturation and germination of individual embryos.

Two different genotypes were used in these experiments: 92B91 and 93B82. Samples of tissue were either bombarded with the hygromycin resistance gene alone or with a 1:1 mixture of the hygromycin resistance gene and the LEC1 construct. Embryogenic cultures generated from 92B91 generally produce transformation events while cultures from 93B82 are much more difficult to transform. For transformation experiments with 92B91, approximately equal numbers of transformants were recovered from bombardments conducted with the LEC1 polynucleotide as without it. Twenty-nine transformants were recovered from the LEC1-treated 92B91 tissue while 27 transformants were recovered from tissue receiving only the hygromycin resistance gene. In contrast, transformants were only recovered from 93B82 tissue receiving the LEC1 polynucleotide (none were recovered from the treatment using only the hygromycin resistance gene). Five transformants were recovered from 93B82 tissue bombarded with the LEC1 polynucleotide while no transformants were recovered from tissue treated with only the hygromycin resistance gene. These results show that the LEC1 polynucleotide will be very valuable for gene transfer to recalcitrant genotypes of soybean.

What is claimed is:

1. An isolated nucleic acid molecule comprising a polynucleotide selected from the group consisting of:
   (a) a polynucleotide which encodes the polypeptide of SEQ ID NO: 22;
   (b) a polynucleotide which encodes a polypeptide having at least 95% sequence identity to SEQ ID NO: 22, wherein the % of sequence identity is determined by GAP analysis using Gap Weight of 50 and Length Weight of 3; and wherein the polypeptide has transcriptional regulatory activity of LEC1 protein;
   (c) a polynucleotide having the sequence set forth in SEQ ID NO: 1; and
   (d) a polynucleotide fully complementary to a polynucleotide of (a) through (c).

2. An expression cassette comprising the isolated nucleic acid molecule of claim 1.

3. A transgenic plant cell comprising the isolated nucleic acid molecule of claim 1.

4. A transgenic plant comprising the isolated nucleic acid molecule of claim 1.

5. A transgenic plant seed comprising the isolated nucleic acid molecule of claim 1.

6. A method for modulating the level of LEC1 protein in a plant, comprising:
   (a) transforming a plant cell with at least one expression cassette comprising at least one isolated nucleic acid molecule comprising a polynucleotide selected from the group consisting of:
      (i) a polynucleotide which encodes the polypeptide of SEQ ID NO: 22
      (ii) a polynucleotide which encodes a polypeptide having at least 95% sequence identity to SEQ ID NO: 22, wherein the % of sequence identity is determined by GAP analysis using Gap Weight of 50 and Length Weight of 3; and wherein the polypeptide has transcriptional regulatory activity of LEC1 protein;
      (iii) a polynucleotide having the sequence set forth in SEQ ID NO: 1; and
      (iv) a polynucleotide fully complementary to a polynucleotide of (i) through (iii); and
   (b) regenerating the transformed plant cell into a transformed plant that expresses the at least one nucleic acid in an amount sufficient to modulate the level of LEC1 protein in the plant.

7. The method of claim 6, wherein the plant is corn, soybean, *sorghum,* wheat, rice, alfalfa, sunflower, canola or cotton.

8. The method of claim 6, wherein the level of LEC1 protein is increased.

9. The method of claim 6, wherein the level of LEC1 protein is decreased.

10. The method of claim 6 wherein the at least one nucleic acid is a ribonucleic acid.

11. A method for modulating the level of LEC1 protein in a plant cell, comprising:
    (a) transforming a plant cell with at least one expression cassette comprising at least one isolated nucleic acid molecule comprising a polynucleotide selected from the group consisting of:
       (i) a polynucleotide which encodes the polypeptide of SEQ ID NO: 22;
       (ii) a polynucleotide which encodes a polypeptide having at least 95% sequence identity to SEQ ID NO: 22, wherein the % of sequence identity is determined by GAP analysis using Gap Weight of 50 and Length Weight of 3; and wherein the polypeptide has transcriptional regulatory activity of LEC1 protein;
       (iii) a polynucleotide having the sequence set forth in SEQ ID NO: 1; and
       (iv) a polynucleotide fully complementary to a polynucleotide of (i) through (iii); and
    (b) expressing the polynucleotide for a time sufficient to modulate the level of LEC1 protein in said plant cell.

12. An isolated polynucleotide having at least 95% sequence identity to the entire coding sequence of SEQ ID NO: 21, wherein the % sequence identity is determined by GAP analysis using Gap Weight of 50 and Length Weight of 3; wherein the polynucleotide encodes a polypeptide having transcriptional regulatory activity of LEC1 protein and comprises SEQ ID NO: 23.

13. An isolated polynucleotide fully complementary to an isolated polynucleotide of claim 12.

* * * * *

UNITED STATES PATENT AND TRADEMARK OFFICE
CERTIFICATE OF CORRECTION

PATENT NO. : 7,166,765 B2 Page 1 of 2
APPLICATION NO. : 10/744620
DATED : January 23, 2007
INVENTOR(S) : Keith S. Lowe et al.

It is certified that error appears in the above-identified patent and that said Letters Patent is hereby corrected as shown below:

Column 75
Lines 8-21 should read as follows:
--1. An isolated nucleic acid molecule comprising a polynucleotide selected from the group consisting of:
   (a) a polynucleotide which encodes the polypeptide of SEQ ID NO: 22;
   (b) a polynucleotide which encodes a polypeptide having at least 95% sequence identity to SEQ ID NO 22, wherein the % sequence identity is determined by GAP analysis using Gap Weight of 50 and Length Weight of 3; and wherein the polypeptide has transcriptional regulatory activity of LEC1 protein;
   (c) a polynucleotide having the sequence set forth in SEQ ID NO: 21; and
   (d) a polynucleotide fully complementary to a polynucleotide of (a) through (c).--

Column 75
Line 30-51 should read as follows:
--6. A method for modulating the level of LEC1 protein in a plant, comprising:
   (a) transforming a plant cell with at least one expression cassette comprising at least one isolated nucleic acid molecule comprising a polynucleotide selected from the group consisting of:
     (i) a polynucleotide which encodes the polypeptide of SEQ ID NO: 22;
     (ii) a polynucleotide which encodes a polypeptide having at least 95% sequence identity SEQ ID NO: 22, wherein the % sequence identity is determined by GAP analysis using Gap Weight of 50 and Length Weight of 3; and wherein the polypeptide has transcriptional regulatory activity of LEC1 protein;
     (iii) a polynucleotide having the sequence set forth in SEQ ID NO: 21; and
     (iv) a polynucleotide fully complementary to a polynucleotide of (i) through (iii); and
   (b) regenerating the transformed plant cell into a transformed plant that expresses the at least one nucleic acid in an amount sufficient to modulate the level of LEC1 protein in the plant.--

Column 76
Lines 18-39 should read as follows:
--11. A method for modulating the level of LEC1 protein in a plant cell, comprising:
   (a) transforming a plant cell with at least one expression cassette comprising at least one isolated nucleic acid molecule comprising a polynucleotide selected from the group consisting of:

UNITED STATES PATENT AND TRADEMARK OFFICE
CERTIFICATE OF CORRECTION

PATENT NO. : 7,166,765 B2 Page 2 of 2
APPLICATION NO. : 10/744620
DATED : January 23, 2007
INVENTOR(S) : Keith S. Lowe et al.

It is certified that error appears in the above-identified patent and that said Letters Patent is hereby corrected as shown below:

<u>Column 76</u>
Lines 18-39 (cont'd)
        (i) a polynucleotide which encodes the polypeptide of SEQ ID NO: 22;
        (ii) a polynucleotide which encodes a polypeptide having at least 95% sequence identity to SEQ ID NO: 22, wherein the % sequence identity is determined by GAP analysis using Gap Weight of 50 and Length Weight of 3; and wherein the polypeptide has transcriptional regulatory activity of LEC1 protein;
        (iii) a polynucleotide having the sequence set forth in SEQ ID NO: 21; and
        (v) a polynucleotide fully complementary to a polynucleotide of (i) through (iii); and
    (b) expressing the polynucleotide for a time sufficient to modulate the level of protein in said plant cell.--

Signed and Sealed this

Tenth Day of April, 2007

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 1173
<212> TYPE: DNA
<213> ORGANISM: Zea mays
<220> FEATURE:
<221> NAME/KEY: CDS
<222> LOCATION: (69)...(902)

<400> SEQUENCE: 1
ccacgcgtcc gccaccacac cacgagcgcg cgataaccct agctagcttc aggtagtagc      60 gagagcca atg gac tcc agc agc ttc ctc cct gcc gcc ggc gcg gag aat     110
        Met Asp Ser Ser Ser Phe Leu Pro Ala Ala Gly Ala Glu Asn
          1               5                  10 ggc tcg gcg gcg ggc ggc gcc aac aat ggc ggc gct gct cag cag cat     158
Gly Ser Ala Ala Gly Gly Ala Asn Asn Gly Gly Ala Ala Gln Gln His
 15                  20                  25                  30 gcg gcg ccg gcg atc cgc gag cag gac cgg ctg atg ccg atc gcg aac     206
Ala Ala Pro Ala Ile Arg Glu Gln Asp Arg Leu Met Pro Ile Ala Asn
                 35                  40                  45
```

| | | | | | | | | | | | | | | | | |
|---|---|---|---|---|---|---|---|---|---|---|---|---|---|---|---|---|
| gtg | atc | cgc | atc | atg | cgg | cgc | gtg | ctg | ccg | gcg | cac | gcc | aag | atc | tcg | 254 |
| Val | Ile | Arg | Ile | Met | Arg | Arg | Val | Leu | Pro | Ala | His | Ala | Lys | Ile | Ser | |
| | | | 50 | | | | | 55 | | | | | 60 | | | |
| gac | gac | gcc | aag | gag | acg | atc | cag | gag | tgc | gtg | tcg | gag | tac | atc | agc | 302 |
| Asp | Asp | Ala | Lys | Glu | Thr | Ile | Gln | Glu | Cys | Val | Ser | Glu | Tyr | Ile | Ser | |
| | | | 65 | | | | 70 | | | | | 75 | | | | |
| ttc | atc | acg | ggg | gag | gcc | aac | gag | cgg | tgc | cag | cgg | gag | cag | cgc | aag | 350 |
| Phe | Ile | Thr | Gly | Glu | Ala | Asn | Glu | Arg | Cys | Gln | Arg | Glu | Gln | Arg | Lys | |
| | | 80 | | | | | 85 | | | | | 90 | | | | |
| acc | atc | acc | gcc | gag | gac | gtg | ctg | tgg | gcc | atg | agc | cgc | ctc | ggc | ttc | 398 |
| Thr | Ile | Thr | Ala | Glu | Asp | Val | Leu | Trp | Ala | Met | Ser | Arg | Leu | Gly | Phe | |
| 95 | | | | | 100 | | | | | 105 | | | | | 110 | |
| gac | gac | tac | gtc | gag | ccg | ctc | ggc | gcc | tac | ctc | cac | cgc | tac | cgc | gag | 446 |
| Asp | Asp | Tyr | Val | Glu | Pro | Leu | Gly | Ala | Tyr | Leu | His | Arg | Tyr | Arg | Glu | |
| | | | | 115 | | | | | 120 | | | | | 125 | | |
| ttc | gag | ggc | gac | gcg | cgc | ggc | gtc | ggg | ctc | gtc | ccg | ggg | gcc | gcc | cca | 494 |
| Phe | Glu | Gly | Asp | Ala | Arg | Gly | Val | Gly | Leu | Val | Pro | Gly | Ala | Ala | Pro | |
| | | | 130 | | | | | 135 | | | | | 140 | | | |
| tcg | cgc | ggc | ggc | gac | cac | cac | ccg | cac | tcc | atg | tcg | cca | gcg | gcg | atg | 542 |
| Ser | Arg | Gly | Gly | Asp | His | His | Pro | His | Ser | Met | Ser | Pro | Ala | Ala | Met | |
| | | | 145 | | | | | 150 | | | | | 155 | | | |
| ctc | aag | tcc | cgc | ggg | cca | gtc | tcc | gga | gcc | gcc | atg | cta | ccg | cac | cac | 590 |
| Leu | Lys | Ser | Arg | Gly | Pro | Val | Ser | Gly | Ala | Ala | Met | Leu | Pro | His | His | |
| | | 160 | | | | | 165 | | | | | 170 | | | | |
| cac | cac | cac | cac | gac | atg | cag | atg | cac | gcc | gcc | atg | tac | ggg | gga | acg | 638 |
| His | His | His | His | Asp | Met | Gln | Met | His | Ala | Ala | Met | Tyr | Gly | Gly | Thr | |
| 175 | | | | | 180 | | | | | 185 | | | | | 190 | |
| gcc | gtg | ccc | ccg | ccg | gcc | ggg | cct | cct | cac | cac | ggc | ggg | ttc | ctc | atg | 686 |
| Ala | Val | Pro | Pro | Pro | Ala | Gly | Pro | Pro | His | His | Gly | Gly | Phe | Leu | Met | |
| | | | | 195 | | | | | 200 | | | | | 205 | | |
| cca | cac | cca | cag | ggt | agt | agc | cac | tac | ctg | cct | tac | gcg | tac | gag | ccc | 734 |
| Pro | His | Pro | Gln | Gly | Ser | Ser | His | Tyr | Leu | Pro | Tyr | Ala | Tyr | Glu | Pro | |
| | | | 210 | | | | | 215 | | | | | 220 | | | |
| acg | tac | ggc | ggt | gag | cac | gcc | atg | gct | gca | tac | tat | gga | ggc | gcc | gcg | 782 |
| Thr | Tyr | Gly | Gly | Glu | His | Ala | Met | Ala | Ala | Tyr | Tyr | Gly | Gly | Ala | Ala | |
| | | | 225 | | | | | 230 | | | | | 235 | | | |
| tac | gcg | ccc | ggc | aac | ggc | ggg | agc | ggc | gac | ggc | agt | ggc | agt | ggc | ggc | 830 |
| Tyr | Ala | Pro | Gly | Asn | Gly | Gly | Ser | Gly | Asp | Gly | Ser | Gly | Ser | Gly | Gly | |
| | 240 | | | | | 245 | | | | | 250 | | | | | |
| ggt | ggc | ggg | agc | gcg | tcg | cac | aca | ccg | cag | ggc | agc | ggc | ggc | ttg | gag | 878 |
| Gly | Gly | Gly | Ser | Ala | Ser | His | Thr | Pro | Gln | Gly | Ser | Gly | Gly | Leu | Glu | |
| 255 | | | | | 260 | | | | | 265 | | | | | 270 | |
| cac | ccg | cac | ccg | ttc | gcg | tac | aag | tagctagttc | gtacgtcgtt | cgacttgagc | | | | | | 932 |
| His | Pro | His | Pro | Phe | Ala | Tyr | Lys | | | | | | | | | |
| | | | | 275 | | | | | | | | | | | | |

| | | |
|---|---|---|
| aagccatcga tctgctgatc tgaacgtacg ctgtattgta cacgcatgca cgtacgtatc | 992 |
| ggcggctagc tctcctgttt aagttgtact gtgattctgt cccggccggc tagcaactta | 1052 |
| gtatcttcct tcagtctcta gtttcttagc agtcgtagaa gtgttcaatg cttgccagtg | 1112 |
| tgttgtttta gggccggggt aaaccatccg atgagattat ttcaaaaaaa aaaaaaaaa | 1172 |
| a | 1173 |

<210> SEQ ID NO 2
<211> LENGTH: 278
<212> TYPE: PRT
<213> ORGANISM: Zea mays

<400> SEQUENCE: 2

-continued

```
Met Asp Ser Ser Ser Phe Leu Pro Ala Ala Gly Ala Glu Asn Gly Ser
 1               5                  10                  15

Ala Ala Gly Gly Ala Asn Asn Gly Gly Ala Ala Gln Gln His Ala Ala
            20                  25                  30

Pro Ala Ile Arg Glu Gln Asp Arg Leu Met Pro Ile Ala Asn Val Ile
        35                  40                  45

Arg Ile Met Arg Arg Val Leu Pro Ala His Ala Lys Ile Ser Asp Asp
 50                  55                  60

Ala Lys Glu Thr Ile Gln Glu Cys Val Ser Glu Tyr Ile Ser Phe Ile
 65                  70                  75                  80

Thr Gly Glu Ala Asn Glu Arg Cys Gln Arg Glu Gln Arg Lys Thr Ile
                85                  90                  95

Thr Ala Glu Asp Val Leu Trp Ala Met Ser Arg Leu Gly Phe Asp Asp
            100                 105                 110

Tyr Val Glu Pro Leu Gly Ala Tyr Leu His Arg Tyr Arg Glu Phe Glu
        115                 120                 125

Gly Asp Ala Arg Gly Val Gly Leu Val Pro Gly Ala Ala Pro Ser Arg
130                 135                 140

Gly Gly Asp His His Pro His Ser Met Ser Pro Ala Ala Met Leu Lys
145                 150                 155                 160

Ser Arg Gly Pro Val Ser Gly Ala Ala Met Leu Pro His His His His
                165                 170                 175

His His Asp Met Gln Met His Ala Ala Met Tyr Gly Gly Thr Ala Val
            180                 185                 190

Pro Pro Pro Ala Gly Pro Pro His His Gly Gly Phe Leu Met Pro His
        195                 200                 205

Pro Gln Gly Ser Ser His Tyr Leu Pro Tyr Ala Tyr Glu Pro Thr Tyr
210                 215                 220

Gly Gly Glu His Ala Met Ala Ala Tyr Tyr Gly Gly Ala Ala Tyr Ala
225                 230                 235                 240

Pro Gly Asn Gly Gly Ser Gly Asp Gly Ser Gly Ser Gly Gly Gly Gly
                245                 250                 255

Gly Ser Ala Ser His Thr Pro Gln Gly Ser Gly Gly Leu Glu His Pro
            260                 265                 270

His Pro Phe Ala Tyr Lys
        275
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tagtagcgag agccaatgga                                           20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gccgggacag aatcacagta                                           20

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tagtagcgag agccaatgga                                                    20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6 cccggccta aaacaacaca                                                     20

<210> SEQ ID NO 7
<211> LENGTH: 481
<212> TYPE: DNA
<213> ORGANISM: Argemone mexicana
<220> FEATURE:
<221> NAME/KEY: CDS
<222> LOCATION: (44)...(481)
<220> FEATURE:
<221> NAME/KEY: misc_feature
<222> LOCATION: (1)...(481)
<223> OTHER INFORMATION: n = A,T,C or G

<400> SEQUENCE: 7
cgagagaaag agttggtgaa gaagaagaag aagttgaaaa gag atg gaa cgt ggt         55
                                              Met Glu Arg Gly
                                                1 ggt ggt ggt ggt ggt agt ggt ggt ggt ttc cat gga tat cag aaa ctc        103
Gly Gly Gly Gly Gly Ser Gly Gly Gly Phe His Gly Tyr Gln Lys Leu
  5                  10                  15                  20 cca aaa tca aac tcc gct gga atg atg ctc tcg gag cta tcg aat aac        151
Pro Lys Ser Asn Ser Ala Gly Met Met Leu Ser Glu Leu Ser Asn Asn
             25                  30                  35 aac aac aat att gac gta aac tct aca tgt act gta cga gag caa gat        199
Asn Asn Asn Ile Asp Val Asn Ser Thr Cys Thr Val Arg Glu Gln Asp
         40                  45                  50 cga tac atg cca att gct aat gtg atc agg atc atg cgt aag gta ctt        247
Arg Tyr Met Pro Ile Ala Asn Val Ile Arg Ile Met Arg Lys Val Leu
     55                  60                  65 cct act cat gcc aag atc tct gac gat gcc aaa gaa act atc caa gaa        295
Pro Thr His Ala Lys Ile Ser Asp Asp Ala Lys Glu Thr Ile Gln Glu
 70                  75                  80 tgt gtc tca gaa tac atc agt ttc atc aca agt gaa gcc aat gat cgt        343
Cys Val Ser Glu Tyr Ile Ser Phe Ile Thr Ser Glu Ala Asn Asp Arg
 85                  90                  95                 100 tgc caa cgt gaa caa aga aag aca atc aca gct gaa gat gtt tta tgg        391
Cys Gln Arg Glu Gln Arg Lys Thr Ile Thr Ala Glu Asp Val Leu Trp
                105                 110                 115 gcg atg agc aaa cta ggg ntt gat gag tac att gaa cct cta act ctt        439
Ala Met Ser Lys Leu Gly Xaa Asp Glu Tyr Ile Glu Pro Leu Thr Leu
                120                 125                 130 tac ctt caa cgt tat cgt gag ttt gaa ggt gna cgt tgg tca                481
Tyr Leu Gln Arg Tyr Arg Glu Phe Glu Gly Xaa Arg Trp Ser
135                 140                 145
```

<210> SEQ ID NO 8
<211> LENGTH: 146
<212> TYPE: PRT
<213> ORGANISM: Argemone mexicana
<220> FEATURE:
<221> NAME/KEY: VARIANT
<222> LOCATION: (1)...(146)
<223> OTHER INFORMATION: Xaa = Any Amino Acid

<400> SEQUENCE: 8

```
Met Glu Arg Gly Gly Gly Gly Gly Ser Gly Gly Gly Phe His Gly
 1               5                  10                  15

Tyr Gln Lys Leu Pro Lys Ser Asn Ser Ala Gly Met Met Leu Ser Glu
                 20                  25                  30

Leu Ser Asn Asn Asn Asn Ile Asp Val Asn Ser Thr Cys Thr Val
             35                  40                  45

Arg Glu Gln Asp Arg Tyr Met Pro Ile Ala Asn Val Ile Arg Ile Met
         50                  55                  60

Arg Lys Val Leu Pro Thr His Ala Lys Ile Ser Asp Asp Ala Lys Glu
 65                  70                  75                  80

Thr Ile Gln Glu Cys Val Ser Glu Tyr Ile Ser Phe Ile Thr Ser Glu
                 85                  90                  95

Ala Asn Asp Arg Cys Gln Arg Glu Gln Arg Lys Thr Ile Thr Ala Glu
                100                 105                 110

Asp Val Leu Trp Ala Met Ser Lys Leu Gly Xaa Asp Glu Tyr Ile Glu
            115                 120                 125

Pro Leu Thr Leu Tyr Leu Gln Arg Tyr Arg Glu Phe Glu Gly Xaa Arg
        130                 135                 140

Trp Ser
145
```

<210> SEQ ID NO 9
<211> LENGTH: 942
<212> TYPE: DNA
<213> ORGANISM: Glycine max
<220> FEATURE:
<221> NAME/KEY: CDS
<222> LOCATION: (3)...(722)

<400> SEQUENCE: 9

```
gc acg agc tct ctt ata atc aca cac aca cct acc tta ata gct atg      47
      Thr Ser Ser Leu Ile Ile Thr His Thr Pro Thr Leu Ile Ala Met
        1               5                  10                  15 gaa act gga ggc ttt cac ggc tac cgc aag ctc ccc aac acc acc gct     95
Glu Thr Gly Gly Phe His Gly Tyr Arg Lys Leu Pro Asn Thr Thr Ala
                 20                  25                  30 ggg ttg aag ctg tca gtg tca gac atg aac atg agg cag cag gta gca    143
Gly Leu Lys Leu Ser Val Ser Asp Met Asn Met Arg Gln Gln Val Ala
             35                  40                  45 tca tca gat cac agt gca gcc aca gga gag gag aac gaa tgc acg gtg    191
Ser Ser Asp His Ser Ala Ala Thr Gly Glu Glu Asn Glu Cys Thr Val
         50                  55                  60 agg gag caa gac agg ttc atg cca atc gcc aac gtg att agg atc atg    239
Arg Glu Gln Asp Arg Phe Met Pro Ile Ala Asn Val Ile Arg Ile Met
 65                  70                  75 cgc aag att ctc cct cca cac gca aaa atc tcg gac gat gca aaa gaa    287
Arg Lys Ile Leu Pro Pro His Ala Lys Ile Ser Asp Asp Ala Lys Glu
         80                  85                  90                  95 aca atc caa gag tgc gtg tct gag tac atc agc ttc atc aca ggt gag    335
Thr Ile Gln Glu Cys Val Ser Glu Tyr Ile Ser Phe Ile Thr Gly Glu
                100                 105                 110
```

-continued

| | | |
|---|---|---|
| gcg aac gag cgt tgc cag agg gag cag cgg aag acc ata acc gca gag<br>Ala Asn Glu Arg Cys Gln Arg Glu Gln Arg Lys Thr Ile Thr Ala Glu<br>115                        120                     125 | | 383 |
| gac gtg ctt tgg gcc atg agc aag ctt gga ttc gac gac tac atc gaa<br>Asp Val Leu Trp Ala Met Ser Lys Leu Gly Phe Asp Asp Tyr Ile Glu<br>         130                     135                     140 | | 431 |
| ccg ttg acc atg tac ctt cac cgc tac cgt gaa ctt gag ggt gac cgc<br>Pro Leu Thr Met Tyr Leu His Arg Tyr Arg Glu Leu Glu Gly Asp Arg<br>145                        150                     155 | | 479 |
| acc tct atg agg ggt gaa cca ctc ggg aag agg act gtg gaa tac gcc<br>Thr Ser Met Arg Gly Glu Pro Leu Gly Lys Arg Thr Val Glu Tyr Ala<br>160                        165                     170                     175 | | 527 |
| acg ctt ggt gtt gct act gct ttt gtc cct cca ccc tat cat cac cac<br>Thr Leu Gly Val Ala Thr Ala Phe Val Pro Pro Pro Tyr His His His<br>         180                     185                     190 | | 575 |
| aat ggg tac ttt ggt gct gcc atg ccc atg ggg act tac gtt agg gaa<br>Asn Gly Tyr Phe Gly Ala Ala Met Pro Met Gly Thr Tyr Val Arg Glu<br>                 195                     200                     205 | | 623 |
| gcg cca cca aat aca gcc tcc tcc cat cac cac cac cac cac cac cac<br>Ala Pro Pro Asn Thr Ala Ser Ser His His His His His His His His<br>210                        215                     220 | | 671 |
| cac cat gct cgt gga atc tcc aat gct cat gaa cca aat gct cgc tcc<br>His His Ala Arg Gly Ile Ser Asn Ala His Glu Pro Asn Ala Arg Ser<br>225                        230                     235 | | 719 |
| ata taaaattata taattatgac taggattcag aacaagactt gatgatgatt<br>Ile<br>240 | | 772 |
| agcttaactc tcagtaattg gtgctagagt actactgttg ttgaggatac tttattttat | | 832 |
| aattaagggc tgggaaggga gttagtatat tcctaatcct aactatgtgc atctttaatt | | 892 |
| tatgaaatca ctttgtttta acctttgatg aaaaaaaaaa aaaaaaaaa | | 942 |

<210> SEQ ID NO 10
<211> LENGTH: 240
<212> TYPE: PRT
<213> ORGANISM: Glycine max

<400> SEQUENCE: 10

Thr Ser Ser Leu Ile Ile Thr His Thr Pro Thr Leu Ile Ala Met Glu
1                    5                     10                   15

Thr Gly Gly Phe His Gly Tyr Arg Lys Leu Pro Asn Thr Thr Ala Gly
                 20                     25                     30

Leu Lys Leu Ser Val Ser Asp Met Asn Met Arg Gln Gln Val Ala Ser
          35                     40                     45

Ser Asp His Ser Ala Ala Thr Gly Glu Glu Asn Glu Cys Thr Val Arg
 50                     55                     60

Glu Gln Asp Arg Phe Met Pro Ile Ala Asn Val Ile Arg Ile Met Arg
65                    70                     75                     80

Lys Ile Leu Pro Pro His Ala Lys Ile Ser Asp Ala Lys Glu Thr
                 85                     90                     95

Ile Gln Glu Cys Val Ser Glu Tyr Ile Ser Phe Ile Thr Gly Glu Ala
                 100                    105                  110

Asn Glu Arg Cys Gln Arg Glu Gln Arg Lys Thr Ile Thr Ala Glu Asp
         115                     120                     125

Val Leu Trp Ala Met Ser Lys Leu Gly Phe Asp Asp Tyr Ile Glu Pro
         130                     135                     140

Leu Thr Met Tyr Leu His Arg Tyr Arg Glu Leu Glu Gly Asp Arg Thr

```
                145                 150                 155                 160
Ser Met Arg Gly Glu Pro Leu Gly Lys Arg Thr Val Glu Tyr Ala Thr
                    165                 170                 175

Leu Gly Val Ala Thr Ala Phe Val Pro Pro Tyr His His His Asn
                180                 185                 190

Gly Tyr Phe Gly Ala Ala Met Pro Met Gly Thr Tyr Val Arg Glu Ala
            195                 200                 205

Pro Pro Asn Thr Ala Ser Ser His His His His His His His
        210                 215                 220

His Ala Arg Gly Ile Ser Asn Ala His Glu Pro Asn Ala Arg Ser Ile
225                 230                 235                 240

<210> SEQ ID NO 11
<211> LENGTH: 905
<212> TYPE: DNA
<213> ORGANISM: Veronia mespilifolia
<220> FEATURE:
<221> NAME/KEY: CDS
<222> LOCATION: (58)...(699)

<400> SEQUENCE: 11
gcacgagcca atttctagag agagaacgag agagaattct ctaaagagga aaaatag atg      60
                                                                 Met
                                                                   1 gaa cgt gga gga ggt ttc cat ggc tac cac agg ctc ccc atc cac cct        108
Glu Arg Gly Gly Gly Phe His Gly Tyr His Arg Leu Pro Ile His Pro
        5                  10                  15 aca tct gga atc caa caa tcg gat atg aag cta aag cta cca gaa atg        156
Thr Ser Gly Ile Gln Gln Ser Asp Met Lys Leu Lys Leu Pro Glu Met
    20                  25                  30 acc aac aat aac tcg tcc act gat gac aat gag tgc acc gtt cga gaa        204
Thr Asn Asn Asn Ser Ser Thr Asp Asp Asn Glu Cys Thr Val Arg Glu
35                  40                  45 cag gac cgc ttc atg ccg ata gca aac gtg atc cgc atc atg cgg aag        252
Gln Asp Arg Phe Met Pro Ile Ala Asn Val Ile Arg Ile Met Arg Lys
50                  55                  60                  65 atc ctt cct cca cat gcc aag atc tct gat gat gcc aaa gag acg atc        300
Ile Leu Pro Pro His Ala Lys Ile Ser Asp Asp Ala Lys Glu Thr Ile
                70                  75                  80 caa gaa tgt gtt tca gag tac att agc ttt gtc aca ggc gag gca aat        348
Gln Glu Cys Val Ser Glu Tyr Ile Ser Phe Val Thr Gly Glu Ala Asn
            85                  90                  95 gac cgc tgc cag cgt gag caa agg aag acc atc aca gct gaa gat gtg        396
Asp Arg Cys Gln Arg Glu Gln Arg Lys Thr Ile Thr Ala Glu Asp Val
        100                 105                 110 ctc tgg gct atg agc aaa ctg gga ttt gat gat tat atc gag ccc ttg        444
Leu Trp Ala Met Ser Lys Leu Gly Phe Asp Asp Tyr Ile Glu Pro Leu
    115                 120                 125 act gtg tat ctc cat cgc tac agg gag ttt gat ggt ggc gaa cgt gga        492
Thr Val Tyr Leu His Arg Tyr Arg Glu Phe Asp Gly Gly Glu Arg Gly
130                 135                 140                 145 tcc ata agg ggt gag ccc ctt gtg aag agg agt act tct gat cct ggt        540
Ser Ile Arg Gly Glu Pro Leu Val Lys Arg Ser Thr Ser Asp Pro Gly
                150                 155                 160 cac ttt ggg atg gct tct ttt gtg cct gct ttt cat atg ggt cat cat        588
His Phe Gly Met Ala Ser Phe Val Pro Ala Phe His Met Gly His His
            165                 170                 175 aac ggc ttc ttt ggt cct gca agc att ggt ggt ttc ctg aaa gac cca        636
Asn Gly Phe Phe Gly Pro Ala Ser Ile Gly Gly Phe Leu Lys Asp Pro
        180                 185                 190
```

```
tcg agt gct ggc cct tcg gga cct gca gtc gct ggg ttt gag ccg tat    684
Ser Ser Ala Gly Pro Ser Gly Pro Ala Val Ala Gly Phe Glu Pro Tyr
    195                 200                 205 gct cag tgt aaa gag taactgcaaa aagtagggggt tgggatgaga tgatgatgat    739
Ala Gln Cys Lys Glu
210 ggtggtggtg gtggtggttt gttttgtttt gttctttctt ttttttttct tctttctttt    799 cttggtcatt gaggaacaaa cttacattgg ttcactttgg ctaggcatgt aaacggttaa    859 catgcttatc aagtagtagt tttcgatcaa aaaaaaaaaa aaaaaa                   905

<210> SEQ ID NO 12
<211> LENGTH: 214
<212> TYPE: PRT
<213> ORGANISM: Veronia mespilifolia

<400> SEQUENCE: 12

Met Glu Arg Gly Gly Gly Phe His Gly Tyr His Arg Leu Pro Ile His
 1               5                  10                  15

Pro Thr Ser Gly Ile Gln Gln Ser Asp Met Lys Leu Lys Leu Pro Glu
            20                  25                  30

Met Thr Asn Asn Asn Ser Ser Thr Asp Asp Asn Glu Cys Thr Val Arg
        35                  40                  45

Glu Gln Asp Arg Phe Met Pro Ile Ala Asn Val Ile Arg Ile Met Arg
    50                  55                  60

Lys Ile Leu Pro Pro His Ala Lys Ile Ser Asp Asp Ala Lys Glu Thr
65                  70                  75                  80

Ile Gln Glu Cys Val Ser Glu Tyr Ile Ser Phe Val Thr Gly Glu Ala
                85                  90                  95

Asn Asp Arg Cys Gln Arg Glu Gln Arg Lys Thr Ile Thr Ala Glu Asp
            100                 105                 110

Val Leu Trp Ala Met Ser Lys Leu Gly Phe Asp Asp Tyr Ile Glu Pro
        115                 120                 125

Leu Thr Val Tyr Leu His Arg Tyr Arg Glu Phe Asp Gly Gly Glu Arg
    130                 135                 140

Gly Ser Ile Arg Gly Glu Pro Leu Val Lys Arg Ser Thr Ser Asp Pro
145                 150                 155                 160

Gly His Phe Gly Met Ala Ser Phe Val Pro Ala Phe His Met Gly His
                165                 170                 175

His Asn Gly Phe Phe Gly Pro Ala Ser Ile Gly Gly Phe Leu Lys Asp
            180                 185                 190

Pro Ser Ser Ala Gly Pro Ser Gly Pro Ala Val Ala Gly Phe Glu Pro
        195                 200                 205

Tyr Ala Gln Cys Lys Glu
    210

<210> SEQ ID NO 13
<211> LENGTH: 763
<212> TYPE: DNA
<213> ORGANISM: Zea mays
<220> FEATURE:
<221> NAME/KEY: CDS
<222> LOCATION: (1)...(480)

<400> SEQUENCE: 13 gca cga ggc aag acc gtc acc tcc gag gac atc gtg tgg gcc atg agc    48
Ala Arg Gly Lys Thr Val Thr Ser Glu Asp Ile Val Trp Ala Met Ser
 1               5                  10                  15
```

-continued

```
cgc ctc ggc ttc gac gac tac gtc gcg ccc ctc ggc gcc ttc ctc cag      96
Arg Leu Gly Phe Asp Asp Tyr Val Ala Pro Leu Gly Ala Phe Leu Gln
         20                  25                  30 cgc atg cgc gac gac agc gac cac ggc ggt gaa gag cgc ggc ggc cct     144
Arg Met Arg Asp Asp Ser Asp His Gly Gly Glu Glu Arg Gly Gly Pro
     35                  40                  45 gca ggg cgt ggt ggc tcg cgc cgc ggc tcg tcg tcc ttg ccg ctc cac     192
Ala Gly Arg Gly Gly Ser Arg Arg Gly Ser Ser Ser Leu Pro Leu His
 50                  55                  60 tgc ccg cag cag atg cac cac ctg cac cca gcc gtc tgc cgg cgt ccg     240
Cys Pro Gln Gln Met His His Leu His Pro Ala Val Cys Arg Arg Pro
 65                  70                  75                  80 cac cag agc gtg tcg cct gct gca gga tac gcc gtc cgg ccc gtt ccc     288
His Gln Ser Val Ser Pro Ala Ala Gly Tyr Ala Val Arg Pro Val Pro
                 85                  90                  95 cgc ccg atg cca gcc cgt ggg tac cgc atg cag ggc gga gac cac cgc     336
Arg Pro Met Pro Ala Arg Gly Tyr Arg Met Gln Gly Gly Asp His Arg
            100                 105                 110 agc gtg ggc ggc gtg gct ccc tgc agc tac gga ggg gcg ctc gtc cag     384
Ser Val Gly Gly Val Ala Pro Cys Ser Tyr Gly Gly Ala Leu Val Gln
        115                 120                 125 gcc ggt gga acc caa cac gtt gtt gga ttc cac gac gac gag gca agc     432
Ala Gly Gly Thr Gln His Val Val Gly Phe His Asp Asp Glu Ala Ser
    130                 135                 140 tct tcg agt gaa aat ccg ccg ccg gag ggg cgt gcc gct ggc tcg aac     480
Ser Ser Ser Glu Asn Pro Pro Pro Glu Gly Arg Ala Ala Gly Ser Asn
145                 150                 155                 160 tagcctagct tctcagttcc ccgtgtacaa taagagggc ggtcgcggcg ccgcgccgcg    540
cccttgggtt gggccgggcg ctatgctgca gtttggtttg taaactaacg agcctagggt    600
agctggtgca cgcgcgccac ctcgccggac gtcgccgtcg tcgtcggcat ggacttaacc    660 ggcgggcccct gttgttattt ctcaagtttg tagccaacga actgttcggt gcgttccata    720
atttaattta ccatgttgct ctcgaaaaaa aaaaaaaaaa aaa                       763
```

<210> SEQ ID NO 14
<211> LENGTH: 160
<212> TYPE: PRT
<213> ORGANISM: Zea mays

<400> SEQUENCE: 14

```
Ala Arg Gly Lys Thr Val Thr Ser Glu Asp Ile Val Trp Ala Met Ser
 1               5                  10                  15

Arg Leu Gly Phe Asp Asp Tyr Val Ala Pro Leu Gly Ala Phe Leu Gln
             20                  25                  30

Arg Met Arg Asp Asp Ser Asp His Gly Gly Glu Glu Arg Gly Gly Pro
         35                  40                  45

Ala Gly Arg Gly Gly Ser Arg Arg Gly Ser Ser Ser Leu Pro Leu His
     50                  55                  60

Cys Pro Gln Gln Met His His Leu His Pro Ala Val Cys Arg Arg Pro
 65                  70                  75                  80

His Gln Ser Val Ser Pro Ala Ala Gly Tyr Ala Val Arg Pro Val Pro
                 85                  90                  95

Arg Pro Met Pro Ala Arg Gly Tyr Arg Met Gln Gly Gly Asp His Arg
            100                 105                 110

Ser Val Gly Gly Val Ala Pro Cys Ser Tyr Gly Gly Ala Leu Val Gln
        115                 120                 125
```

```
Ala Gly Gly Thr Gln His Val Gly Phe His Asp Asp Glu Ala Ser
            130                 135                 140

Ser Ser Ser Glu Asn Pro Pro Glu Gly Arg Ala Ala Gly Ser Asn
145                 150                 155                 160

<210> SEQ ID NO 15
<211> LENGTH: 622
<212> TYPE: DNA
<213> ORGANISM: Zea mays
<220> FEATURE:
<221> NAME/KEY: CDS
<222> LOCATION: (3)...(622)
<220> FEATURE:
<221> NAME/KEY: misc_feature
<222> LOCATION: (1)...(622)
<223> OTHER INFORMATION: n = A,T,C or G

<400> SEQUENCE: 15 gc atg aat aat ccc caa aac cct aaa gcc agt gct cct tgc acc ttg         47
   Met Asn Asn Pro Gln Asn Pro Lys Ala Ser Ala Pro Cys Thr Leu
     1               5                  10                  15 cca ccg gag ctt ccc aaa gaa gca gtg gcg acc gac gaa gca ccg ccg        95
Pro Pro Glu Leu Pro Lys Glu Ala Val Ala Thr Asp Glu Ala Pro Pro
             20                  25                  30 cca atg ggc aac aac aac aac acg gaa tcg gcg acg gcg acg atg gtc       143
Pro Met Gly Asn Asn Asn Asn Thr Glu Ser Ala Thr Ala Thr Met Val
         35                  40                  45 cgg gag cag gac cgg ctg atg ccc gtg gcc aac gtg tcc cgc atc atg       191
Arg Glu Gln Asp Arg Leu Met Pro Val Ala Asn Val Ser Arg Ile Met
     50                  55                  60 cgc caa gtg ctg cct ccg tac gcc aag atc tcc gac gac gcc can gaa       239
Arg Gln Val Leu Pro Pro Tyr Ala Lys Ile Ser Asp Asp Ala Xaa Glu
 65                  70                  75 gtn atc caa gaa ttg ctn ttc gga att tca tca ctt ncg tcc tgg cga       287
Xaa Ile Gln Glu Leu Xaa Phe Gly Ile Ser Ser Leu Xaa Ser Trp Arg
 80                  85                  90                  95 ggc gaa acg aag cgg tgc cac acc gag cgc cgc aag acc gtc acc tcc       335
Gly Glu Thr Lys Arg Cys His Thr Glu Arg Arg Lys Thr Val Thr Ser
                100                 105                 110 gaa gac atc gtg tgg gcc atg agc cgc ctc ggc ttc gac gac tac gtc       383
Glu Asp Ile Val Trp Ala Met Ser Arg Leu Gly Phe Asp Asp Tyr Val
            115                 120                 125 gcg ccc ctc ggc gcc ttc ctc cag cgc atg cgc gac nac agc gaa cac       431
Ala Pro Leu Gly Ala Phe Leu Gln Arg Met Arg Asp Xaa Ser Glu His
        130                 135                 140 ggg ggt gaa aac gcg gcg gcc tgc ang ggg tng tgg tcn cgc cgc ggg       479
Gly Gly Glu Asn Ala Ala Ala Cys Xaa Gly Xaa Trp Xaa Arg Arg Gly
145                 150                 155 tcg tct nct tgg cgc tcc ctt gcc gca ana gat gac aac ttg cac caa       527
Ser Ser Xaa Trp Arg Ser Leu Ala Ala Xaa Asp Asp Asn Leu His Gln
160                 165                 170                 175 acg tct gcc ggg ntc gga cca aaa ctn ttc cct gtt gca gga ata ccc       575
Thr Ser Ala Gly Xaa Gly Pro Lys Xaa Phe Pro Val Ala Gly Ile Pro
                180                 185                 190 gtc cng ggc cnt tcc ccc ccn aat cca acc att tgg ttt ccc ctt gc        622
Val Xaa Gly Xaa Ser Pro Xaa Asn Pro Thr Ile Trp Phe Pro Leu
            195                 200                 205

<210> SEQ ID NO 16
<211> LENGTH: 206
<212> TYPE: PRT
<213> ORGANISM: Zea mays
<220> FEATURE:
```

<221> NAME/KEY: VARIANT
<222> LOCATION: (1)...(206)
<223> OTHER INFORMATION: Xaa = Any Amino Acid

<400> SEQUENCE: 16

```
Met Asn Asn Pro Gln Asn Pro Lys Ala Ser Ala Pro Cys Thr Leu Pro
 1               5                  10                  15

Pro Glu Leu Pro Lys Glu Ala Val Ala Thr Asp Glu Ala Pro Pro
            20                  25                  30

Met Gly Asn Asn Asn Asn Thr Glu Ser Ala Thr Ala Thr Met Val Arg
             35                  40                  45

Glu Gln Asp Arg Leu Met Pro Val Ala Asn Val Ser Arg Ile Met Arg
 50                  55                  60

Gln Val Leu Pro Pro Tyr Ala Lys Ile Ser Asp Asp Ala Xaa Glu Xaa
 65                  70                  75                  80

Ile Gln Glu Leu Xaa Phe Gly Ile Ser Ser Leu Xaa Ser Trp Arg Gly
                 85                  90                  95

Glu Thr Lys Arg Cys His Thr Glu Arg Arg Lys Thr Val Thr Ser Glu
            100                 105                 110

Asp Ile Val Trp Ala Met Ser Arg Leu Gly Phe Asp Asp Tyr Val Ala
            115                 120                 125

Pro Leu Gly Ala Phe Leu Gln Arg Met Arg Asp Xaa Ser Glu His Gly
130                 135                 140

Gly Glu Asn Ala Ala Ala Cys Xaa Gly Xaa Trp Xaa Arg Arg Gly Ser
145                 150                 155                 160

Ser Xaa Trp Arg Ser Leu Ala Ala Xaa Asp Asp Asn Leu His Gln Thr
            165                 170                 175

Ser Ala Gly Xaa Gly Pro Lys Xaa Phe Pro Val Ala Gly Ile Pro Val
            180                 185                 190

Xaa Gly Xaa Ser Pro Xaa Asn Pro Thr Ile Trp Phe Pro Leu
            195                 200                 205
```

<210> SEQ ID NO 17
<211> LENGTH: 1121
<212> TYPE: DNA
<213> ORGANISM: Glycine max
<220> FEATURE:
<221> NAME/KEY: CDS
<222> LOCATION: (3)...(1121)

<400> SEQUENCE: 17

```
gc acg agg gaa act gga ggc ttt cat ggc tac cgc aag ctc ccc aac          47
   Thr Arg Glu Thr Gly Gly Phe His Gly Tyr Arg Lys Leu Pro Asn
    1               5                  10                  15 aca acc tct ggg ttg aag ctg tca gtg tca gac atg aac atg aac atg         95
Thr Thr Ser Gly Leu Lys Leu Ser Val Ser Asp Met Asn Met Asn Met
             20                  25                  30 agg cag cag cag gta gca tca tca gat cag aac tgc agc aac cac agt        143
Arg Gln Gln Gln Val Ala Ser Ser Asp Gln Asn Cys Ser Asn His Ser
         35                  40                  45 gca gca gga gag gag aac gaa tgc acg gtg agg gag caa gac agg ttc        191
Ala Ala Gly Glu Glu Asn Glu Cys Thr Val Arg Glu Gln Asp Arg Phe
 50                  55                  60 atg cca atc gct aac gtg ata cgg atc atg cgc aag att ctc cct cca        239
Met Pro Ile Ala Asn Val Ile Arg Ile Met Arg Lys Ile Leu Pro Pro
 65                  70                  75 cac gca aaa atc tcc gat gat gca aag gag aca atc caa gag tgc gtg        287
His Ala Lys Ile Ser Asp Asp Ala Lys Glu Thr Ile Gln Glu Cys Val
 80                  85                  90                  95
```

```
tcg gag tac atc agc ttc atc acc ggg gag gcc aac gag cgt tgc cag       335
Ser Glu Tyr Ile Ser Phe Ile Thr Gly Glu Ala Asn Glu Arg Cys Gln
            100                 105                 110 agg gag cag cgc aag acc ata acc gca gag gac gtg ctt tgg gca atg       383
Arg Glu Gln Arg Lys Thr Ile Thr Ala Glu Asp Val Leu Trp Ala Met
        115                 120                 125 agt aag ctt gga ttc gac gac tac atc gaa ccg tta acc atg tac ctt       431
Ser Lys Leu Gly Phe Asp Asp Tyr Ile Glu Pro Leu Thr Met Tyr Leu
    130                 135                 140 cac cgc tac cgt gag ctg gag ggt gac cgc acc tct atg agg ggt gaa       479
His Arg Tyr Arg Glu Leu Glu Gly Asp Arg Thr Ser Met Arg Gly Glu
145                 150                 155 ccg ctc ggg aag agg act gtg gaa tat gcc acg ctt gct act gct ttt       527
Pro Leu Gly Lys Arg Thr Val Glu Tyr Ala Thr Leu Ala Thr Ala Phe
160                 165                 170                 175 gtg ccg cca ccc ttt cat cac cac aat ggc tac ttt ggt gct gcc atg       575
Val Pro Pro Pro Phe His His His Asn Gly Tyr Phe Gly Ala Ala Met
            180                 185                 190 ccc atg ggg act tac gtt agg gaa acg cca cca aat gct gcg tca tct       623
Pro Met Gly Thr Tyr Val Arg Glu Thr Pro Pro Asn Ala Ala Ser Ser
        195                 200                 205 cat cac cat cat gga atc tcc aat gct cat gaa cca aat gct cgc tcc       671
His His His His Gly Ile Ser Asn Ala His Glu Pro Asn Ala Arg Ser
    210                 215                 220 ata taa aat taa tga aga gta ctg ttc agt agg aga aca aga ctt ctt       719
Ile  *  Asn  *   *  Arg Val Leu Phe Ser Arg Arg Thr Arg Leu Leu
                225                 230                 235 gga ctt gat tag ctt aac tct cag tga ttg gtg tta gag tac tgt tgt       767
Gly Leu Asp  *  Leu Asn Ser Gln  *  Leu Val Leu Glu Tyr Cys Cys
                    240                 245                 250 tga gga tgg tta att tta taa tta agg gct ggg aat tgg gga gtt agt       815
 *  Gly Trp Leu Ile Leu  *  Leu Arg Ala Gly Asn Trp Gly Val Ser
                    255                 260 ata tat tcc taa tcc taa tta tgt gca tct tta att tat gga ata act       863
Ile Tyr Ser  *  Ser  *  Leu Cys Ala Ser Leu Ile Tyr Gly Ile Thr
265                 270                 275 ttg ttt ttt gtt tta act tct gat aat ttg gat ttt ctg atg ttt aat       911
Leu Phe Phe Val Leu Thr Ser Asp Asn Leu Asp Phe Leu Met Phe Asn
        280                 285                 290 gtg gtt ttg tct atc cct tat taa cag tgc caa gct taa ggt ttt agc       959
Val Val Leu Ser Ile Pro Tyr  *  Gln Cys Gln Ala  *  Gly Phe Ser
295                 300                 305 cat gct cca aaa tgg aat act tgt act gtt atg ttg ttc tgg tag tga      1007
His Ala Pro Lys Trp Asn Thr Cys Thr Val Met Leu Phe Trp  *   *
        310                 315                 320 tgg tga tga aac ctg caa gtt atg ttt atg tat aaa gcc act att gat      1055
Trp  *   *  Asn Leu Gln Val Met Phe Met Tyr Lys Ala Thr Ile Asp
                325                 330                 335 caa aat tag aga aat tat cat tta ata agt atc ctc cca tgt taa ttt      1103
Gln Asn  *  Arg Asn Tyr His Leu Ile Ser Ile Leu Pro Cys  *  Phe
                340                 345                 350 taa aaa aaa aaa aaa aaa                                              1121
 *  Lys Lys Lys Lys Lys
        355
```

<210> SEQ ID NO 18
<211> LENGTH: 355
<212> TYPE: PRT
<213> ORGANISM: Glycine max

<400> SEQUENCE: 18

```
Thr Arg Glu Thr Gly Gly Phe His Gly Tyr Arg Lys Leu Pro Asn Thr
  1               5                  10                  15
Thr Ser Gly Leu Lys Leu Ser Val Ser Asp Met Asn Met Asn Met Arg
             20                  25                  30
Gln Gln Gln Val Ala Ser Ser Asp Gln Asn Cys Ser Asn His Ser Ala
         35                  40                  45
Ala Gly Glu Glu Asn Glu Cys Thr Val Arg Glu Gln Asp Arg Phe Met
 50                  55                  60
Pro Ile Ala Asn Val Ile Arg Ile Met Arg Lys Ile Leu Pro Pro His
 65                  70                  75                  80
Ala Lys Ile Ser Asp Asp Ala Lys Glu Thr Ile Gln Glu Cys Val Ser
                 85                  90                  95
Glu Tyr Ile Ser Phe Ile Thr Gly Glu Ala Asn Glu Arg Cys Gln Arg
            100                 105                 110
Glu Gln Arg Lys Thr Ile Thr Ala Glu Asp Val Leu Trp Ala Met Ser
        115                 120                 125
Lys Leu Gly Phe Asp Asp Tyr Ile Glu Pro Leu Thr Met Tyr Leu His
    130                 135                 140
Arg Tyr Arg Glu Leu Glu Gly Asp Arg Thr Ser Met Arg Gly Glu Pro
145                 150                 155                 160
Leu Gly Lys Arg Thr Val Glu Tyr Ala Thr Leu Ala Thr Ala Phe Val
                165                 170                 175
Pro Pro Pro Phe His His His Asn Gly Tyr Phe Gly Ala Ala Met Pro
            180                 185                 190
Met Gly Thr Tyr Val Arg Glu Thr Pro Pro Asn Ala Ala Ser Ser His
        195                 200                 205
His His His Gly Ile Ser Asn Ala His Glu Pro Asn Ala Arg Ser Ile
    210                 215                 220
Asn Arg Val Leu Phe Ser Arg Arg Thr Arg Leu Leu Gly Leu Asp Leu
225                 230                 235                 240
Asn Ser Gln Leu Val Leu Glu Tyr Cys Cys Gly Trp Leu Ile Leu Leu
                245                 250                 255
Arg Ala Gly Asn Trp Gly Val Ser Ile Tyr Ser Ser Leu Cys Ala Ser
            260                 265                 270
Leu Ile Tyr Gly Ile Thr Leu Phe Phe Val Leu Thr Ser Asp Asn Leu
        275                 280                 285
Asp Phe Leu Met Phe Asn Val Val Leu Ser Ile Pro Tyr Gln Cys Gln
    290                 295                 300
Ala Gly Phe Ser His Ala Pro Lys Trp Asn Thr Cys Thr Val Met Leu
305                 310                 315                 320
Phe Trp Trp Asn Leu Gln Val Met Phe Met Tyr Lys Ala Thr Ile Asp
                325                 330                 335
Gln Asn Arg Asn Tyr His Leu Ile Ser Ile Leu Pro Cys Phe Lys Lys
            340                 345                 350
Lys Lys Lys
    355
```

<210> SEQ ID NO 19
<211> LENGTH: 796
<212> TYPE: DNA
<213> ORGANISM: Glycine max
<220> FEATURE:
<221> NAME/KEY: CDS
<222> LOCATION: (1)...(513)

<400> SEQUENCE: 19

```
gca cga gca atg gcg gga gtg agg gaa cag gac cag tac atg ccg ata    48
Ala Arg Ala Met Ala Gly Val Arg Glu Gln Asp Gln Tyr Met Pro Ile
 1               5                  10                  15 gcg aac gtg ata agg atc atg cgt cgg att ctg cca gcg cac gcg aag    96
Ala Asn Val Ile Arg Ile Met Arg Arg Ile Leu Pro Ala His Ala Lys
             20                  25                  30 atc tca gac gac gcg aag gag acg atc cag gag tgc gtg tct gag tac   144
Ile Ser Asp Asp Ala Lys Glu Thr Ile Gln Glu Cys Val Ser Glu Tyr
         35                  40                  45 atc agt ttc atc acg gcg gag gcg aac gag cgg tgc cag cgg gag cag   192
Ile Ser Phe Ile Thr Ala Glu Ala Asn Glu Arg Cys Gln Arg Glu Gln
 50                  55                  60 cgg aag acg gtg acc gca gag gat gtg ttg tgg gcg atg gag aag ctt   240
Arg Lys Thr Val Thr Ala Glu Asp Val Leu Trp Ala Met Glu Lys Leu
 65                  70                  75                  80 ggc ttt gac aac tac gct cac cct ctc tct ctt tac ctt cac cgc tac   288
Gly Phe Asp Asn Tyr Ala His Pro Leu Ser Leu Tyr Leu His Arg Tyr
                 85                  90                  95 cgc gag agt gaa gga gaa cct gct tct gtc aga cgc gct tct tct gca   336
Arg Glu Ser Glu Gly Glu Pro Ala Ser Val Arg Arg Ala Ser Ser Ala
            100                 105                 110 atg ggg atc aat aat aat atg gtg cac cca cct tat att aat tct cat   384
Met Gly Ile Asn Asn Asn Met Val His Pro Pro Tyr Ile Asn Ser His
        115                 120                 125 ggc ttt gga atg ttt gat ttt gac cca tca tcg caa ggg ttt tac agg   432
Gly Phe Gly Met Phe Asp Phe Asp Pro Ser Ser Gln Gly Phe Tyr Arg
    130                 135                 140 gac gat cat aac gct gct tct gga tct ggt ggt ttt gtt gcg cct ttt   480
Asp Asp His Asn Ala Ala Ser Gly Ser Gly Gly Phe Val Ala Pro Phe
145                 150                 155                 160 gat cct tat gct aac atc aaa cgt gat gcc ctg tgatcatgta agaacaacaa   533
Asp Pro Tyr Ala Asn Ile Lys Arg Asp Ala Leu
                165                 170 ctagtgcatg ctgcttttc acttggttag ttatattcaa gcacaagcac atgcaggtgc   593
agctgcaact atttagcttc atctacaaat cttttttcct ctcttcttct catgctttaa   653
ttatttagag acaatacttg ttattcattg ttatgctcaa ttgctagctt ctattcatcg   713
tcgactgtct gtattgttga tgttcattac agtaacagat aagatggtaa ctgctttact   773
acttcaaaaa aaaaaaaaaa aaa                                          796
```

<210> SEQ ID NO 20
<211> LENGTH: 171
<212> TYPE: PRT
<213> ORGANISM: Glycine max

<400> SEQUENCE: 20

```
Ala Arg Ala Met Ala Gly Val Arg Glu Gln Asp Gln Tyr Met Pro Ile
 1               5                  10                  15

Ala Asn Val Ile Arg Ile Met Arg Arg Ile Leu Pro Ala His Ala Lys
             20                  25                  30

Ile Ser Asp Asp Ala Lys Glu Thr Ile Gln Glu Cys Val Ser Glu Tyr
         35                  40                  45

Ile Ser Phe Ile Thr Ala Glu Ala Asn Glu Arg Cys Gln Arg Glu Gln
 50                  55                  60

Arg Lys Thr Val Thr Ala Glu Asp Val Leu Trp Ala Met Glu Lys Leu
 65                  70                  75                  80
```

```
Gly Phe Asp Asn Tyr Ala His Pro Leu Ser Leu Tyr Leu His Arg Tyr
                85                  90                  95

Arg Glu Ser Glu Gly Glu Pro Ala Ser Val Arg Arg Ala Ser Ser Ala
            100                 105                 110

Met Gly Ile Asn Asn Asn Met Val His Pro Pro Tyr Ile Asn Ser His
        115                 120                 125

Gly Phe Gly Met Phe Asp Phe Asp Pro Ser Ser Gln Gly Phe Tyr Arg
    130                 135                 140

Asp Asp His Asn Ala Ala Ser Gly Ser Gly Phe Val Ala Pro Phe
145                 150                 155                 160

Asp Pro Tyr Ala Asn Ile Lys Arg Asp Ala Leu
                165                 170

<210> SEQ ID NO 21
<211> LENGTH: 1098
<212> TYPE: DNA
<213> ORGANISM: Triticum aestivum
<220> FEATURE:
<221> NAME/KEY: CDS
<222> LOCATION: (55)...(894)

<400> SEQUENCE: 21
```

| | | |
|---|---|---|
| gcacgagcaa gtgcgagtgc gactacctgc attgcacctt ggctagccct agac atg<br>                                                                                                               Met<br>                                                                                                               1 | 57 |

```
gag aac gac ggc gtc ccc aac gga cca gcg gcg ccg gca cct acc cag    105
Glu Asn Asp Gly Val Pro Asn Gly Pro Ala Ala Pro Ala Pro Thr Gln
        5                   10                  15 ggg acg ccg gtg gtg cgg gag cag gac cgg ctg atg ccg atc gcg aac    153
Gly Thr Pro Val Val Arg Glu Gln Asp Arg Leu Met Pro Ile Ala Asn
    20                  25                  30 gtg atc cgc atc atg cgc cgt gcg ctc cct gcc cac gcc aag atc tcc    201
Val Ile Arg Ile Met Arg Arg Ala Leu Pro Ala His Ala Lys Ile Ser
35                  40                  45 gac gac gcc aag gag gcg att cag gaa tgc gtg tcc gag ttc atc agc    249
Asp Asp Ala Lys Glu Ala Ile Gln Glu Cys Val Ser Glu Phe Ile Ser
50                  55                  60                  65 ttc gtc acc ggc gag gcc aac gaa cgg tgc cgc atg cag cac cgc aag    297
Phe Val Thr Gly Glu Ala Asn Glu Arg Cys Arg Met Gln His Arg Lys
            70                  75                  80 acc gtc aac gcc gaa gac atc gtg tgg gcc cta aac cgc ctc ggc ttc    345
Thr Val Asn Ala Glu Asp Ile Val Trp Ala Leu Asn Arg Leu Gly Phe
        85                  90                  95 gac gac tac gtc gtg ccc ctc agc gtc ttc ctg cac cgc atg cgc gac    393
Asp Asp Tyr Val Val Pro Leu Ser Val Phe Leu His Arg Met Arg Asp
    100                 105                 110 ccc gag gcg ggg aca ggt ggt gcc gct gca ggc gac agc cgc gcc gtg    441
Pro Glu Ala Gly Thr Gly Gly Ala Ala Ala Gly Asp Ser Arg Ala Val
115                 120                 125 acg agt gcg cct ccc cgc gcg gcc ccg ccc gtg atc cac gcc gtg ccg    489
Thr Ser Ala Pro Pro Arg Ala Ala Pro Pro Val Ile His Ala Val Pro
130                 135                 140                 145 ctg cag gct cag cgc ccg atg tac gcg ccc ccg gct ccg ttg cag gtt    537
Leu Gln Ala Gln Arg Pro Met Tyr Ala Pro Pro Ala Pro Leu Gln Val
                150                 155                 160 gag aat cag atg cag cgg cct gtg tac gct ccc ccg gct ccg gtg cag    585
Glu Asn Gln Met Gln Arg Pro Val Tyr Ala Pro Pro Ala Pro Val Gln
            165                 170                 175 gtt cag atg cag cgg ggc atc tat ggg ccc cgg gct cca gtg cac ggg    633
```

-continued

```
Val Gln Met Gln Arg Gly Ile Tyr Gly Pro Arg Ala Pro Val His Gly
            180                 185                 190 tac gcc gtc gga atg gcg ccc gtg cgg gcc aac gtc ggc ggg cag tac       681
Tyr Ala Val Gly Met Ala Pro Val Arg Ala Asn Val Gly Gly Gln Tyr
195                 200                 205 cag gtg ttc ggc gga gag ggt gtc atg gcc cag caa tac tac ggg tac       729
Gln Val Phe Gly Gly Glu Gly Val Met Ala Gln Gln Tyr Tyr Gly Tyr
210                 215                 220                 225 ggg tac gag gaa gga gcg tac ggc gca ggt agc agc aac gga gga gcc       777
Gly Tyr Glu Glu Gly Ala Tyr Gly Ala Gly Ser Ser Asn Gly Gly Ala
            230                 235                 240 gcc att ggc gac gag gag agc tcg tcc aac ggc gtg ccg gca ccg ggg       825
Ala Ile Gly Asp Glu Glu Ser Ser Ser Asn Gly Val Pro Ala Pro Gly
            245                 250                 255 gag ggc atg ggg gag cca gag cca gag cca gca gca gaa gaa tcg cat       873
Glu Gly Met Gly Glu Pro Glu Pro Glu Pro Ala Ala Glu Glu Ser His
            260                 265                 270 gac aag ccc gtc caa tct ggc tagtcgcgtg cgcggcgcgc gttagcttct          924
Asp Lys Pro Val Gln Ser Gly
275                 280 gcgtcctgtg tactgtaata atttgccgtg tcgatccggc catggtttgt gtgtgcgtag     984
tgcttatcta atgtgggctt gtcctctagt aattcatgta ttgcttatct aatgtggact    1044
tgtcctctag taattcatgt actctttgct gttgaaaaaa aaaaaaaaaa aaaa          1098

<210> SEQ ID NO 22
<211> LENGTH: 280
<212> TYPE: PRT
<213> ORGANISM: Triticum aestivum

<400> SEQUENCE: 22

Met Glu Asn Asp Gly Val Pro Asn Gly Pro Ala Ala Pro Ala Pro Thr
1               5                   10                  15

Gln Gly Thr Pro Val Val Arg Glu Gln Asp Arg Leu Met Pro Ile Ala
            20                  25                  30

Asn Val Ile Arg Ile Met Arg Arg Ala Leu Pro Ala His Ala Lys Ile
        35                  40                  45

Ser Asp Asp Ala Lys Glu Ala Ile Gln Glu Cys Val Ser Glu Phe Ile
    50                  55                  60

Ser Phe Val Thr Gly Glu Ala Asn Glu Arg Cys Arg Met Gln His Arg
65                  70                  75                  80

Lys Thr Val Asn Ala Glu Asp Ile Val Trp Ala Leu Asn Arg Leu Gly
                85                  90                  95

Phe Asp Asp Tyr Val Val Pro Leu Ser Val Phe Leu His Arg Met Arg
            100                 105                 110

Asp Pro Glu Ala Gly Thr Gly Gly Ala Ala Ala Gly Asp Ser Arg Ala
        115                 120                 125

Val Thr Ser Ala Pro Pro Arg Ala Pro Pro Val Ile His Ala Val
    130                 135                 140

Pro Leu Gln Ala Gln Arg Pro Met Tyr Ala Pro Pro Ala Pro Leu Gln
145                 150                 155                 160

Val Glu Asn Gln Met Gln Arg Pro Val Tyr Ala Pro Pro Ala Pro Val
                165                 170                 175

Gln Val Gln Met Gln Arg Gly Ile Tyr Gly Pro Arg Ala Pro Val His
            180                 185                 190

Gly Tyr Ala Val Gly Met Ala Pro Val Arg Ala Asn Val Gly Gly Gln
        195                 200                 205
```

-continued

```
Tyr Gln Val Phe Gly Gly Glu Gly Val Met Ala Gln Gln Tyr Tyr Gly
    210                 215                 220

Tyr Gly Tyr Glu Glu Gly Ala Tyr Gly Ala Gly Ser Ser Asn Gly Gly
225                 230                 235                 240

Ala Ala Ile Gly Asp Glu Glu Ser Ser Asn Gly Val Pro Ala Pro
                245                 250                 255

Gly Glu Gly Met Gly Glu Pro Glu Pro Glu Pro Ala Ala Glu Glu Ser
            260                 265                 270

His Asp Lys Pro Val Gln Ser Gly
        275                 280

<210> SEQ ID NO 23
<211> LENGTH: 65
<212> TYPE: PRT
<213> ORGANISM: Artificial Sequence
<220> FEATURE:
<223> OTHER INFORMATION: LEC1 consensus protein sequence
<220> FEATURE:
<221> NAME/KEY: VARIANT
<222> LOCATION: (1)...(65)
<223> OTHER INFORMATION: Xaa = Any Amino Acid

<400> SEQUENCE: 23

Arg Glu Gln Asp Xaa Xaa Met Pro Ile Ala Asn Val Ile Arg Ile Met
1               5                   10                  15

Arg Xaa Xaa Leu Pro Xaa His Ala Lys Ile Ser Asp Asp Ala Lys Glu
            20                  25                  30

Xaa Ile Gln Glu Cys Val Ser Glu Tyr Ile Ser Phe Xaa Thr Xaa Glu
        35                  40                  45

Ala Asn Xaa Arg Cys Xaa Xaa Xaa Xaa Arg Lys Thr Xaa Xaa Xaa Glu
    50                  55                  60

Xaa
65

<210> SEQ ID NO 24
<211> LENGTH: 36
<212> TYPE: DNA
<213> ORGANISM: Artificial Sequence
<220> FEATURE:
<223> OTHER INFORMATION: Sal-A20 oligo

<400> SEQUENCE: 24
tcgacccacg cgtccgaaaa aaaaaaaaaa aaaaaa                          36

<210> SEQ ID NO 25
<211> LENGTH: 22
<212> TYPE: DNA
<213> ORGANISM: Artificial Sequence
<220> FEATURE:
<223> OTHER INFORMATION: primer-forward

<400> SEQUENCE: 25
cgctctgtca cctgttgtac tc                                         22

<210> SEQ ID NO 26
<211> LENGTH: 22
<212> TYPE: DNA
<213> ORGANISM: Artificial Sequence
<220> FEATURE:
<223> OTHER INFORMATION: primer-reverse

<400> SEQUENCE: 26
```

```
cgtgatgaag ctgatgtact cc                                              22
```